United States Patent [19]

Fiers et al.

[11] Patent Number: 5,401,642
[45] Date of Patent: Mar. 28, 1995

[54] VECTORS AND METHODS FOR MAKING SUCH VECTORS AND FOR EXPRESSING CLONED GENES

[75] Inventors: Walter C. Fiers, Destelbergen; Erik R. Remaut, Vinderhoute, both of Belgium

[73] Assignee: Biogen, Inc., Cambridge, Mass.

[21] Appl. No.: 59,193

[22] Filed: May 7, 1993

Related U.S. Application Data

[60] Continuation of Ser. No. 387,505, Jul. 28, 1989, abandoned, which is a division of Ser. No. 921,803, Oct. 20, 1986, Pat. No. 4,874,702, which is a continuation of Ser. No. 250,608, Apr. 3, 1981, abandoned.

[30] Foreign Application Priority Data

Sep. 8, 1980 [GB] United Kingdom ................ 8028983

[51] Int. Cl.⁶ .................... C12P 21/00; C12P 21/02
[52] U.S. Cl. ................... 435/69.1; 435/69.5; 435/69.51; 435/69.52; 435/69.6; 435/320.1
[58] Field of Search ................ 435/69.1-69.9, 435/172.3, 320.1, 240.1, 240.2, 252.3-252.35; 935/39, 40, 41, 44, 45; 536/24.1

[56] References Cited

PUBLICATIONS

Roberts et al; Proc. Natl. Acad. Sci. USA 76: 760 (1979).

*Primary Examiner*—James Martinell
*Attorney, Agent, or Firm*—James F. Haley, Jr.; John J. Cassingham

[57] ABSTRACT

Improved vectors and methods for expressing cloned genes of prokaryotic or eukaryotic origin and methods of making such vectors are disclosed, the improved vectors comprising promoters and operators from λ phages and preferably do not include an active cro gene or an active N gene, the vectors having at least one endonuclease recognition site for cloning desired genes less than about 300 base pairs from the promoters and operators and being useful, as are methods utilizing the vectors, in producing a wide variety of prokaryotic, eukaryotic and vital polypeptides, hormones, enzymes, antigens, proteins and amino acids.

3 Claims, 14 Drawing Sheets

FIG. 6

LAMBDA PROMOTER P_L

FIG. 8A
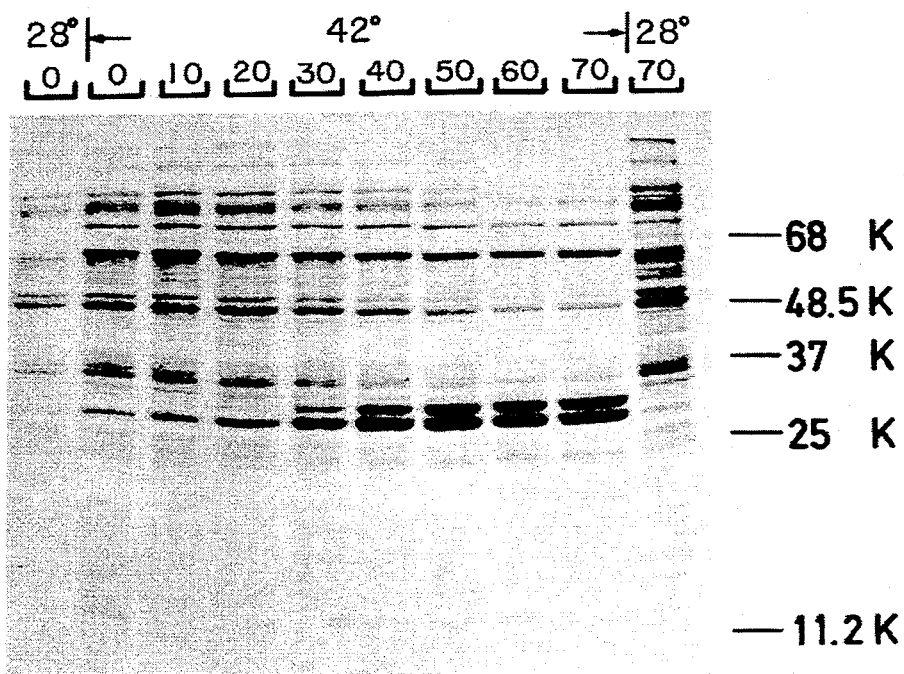
E.coli K12 ΔHI (pPLa23)
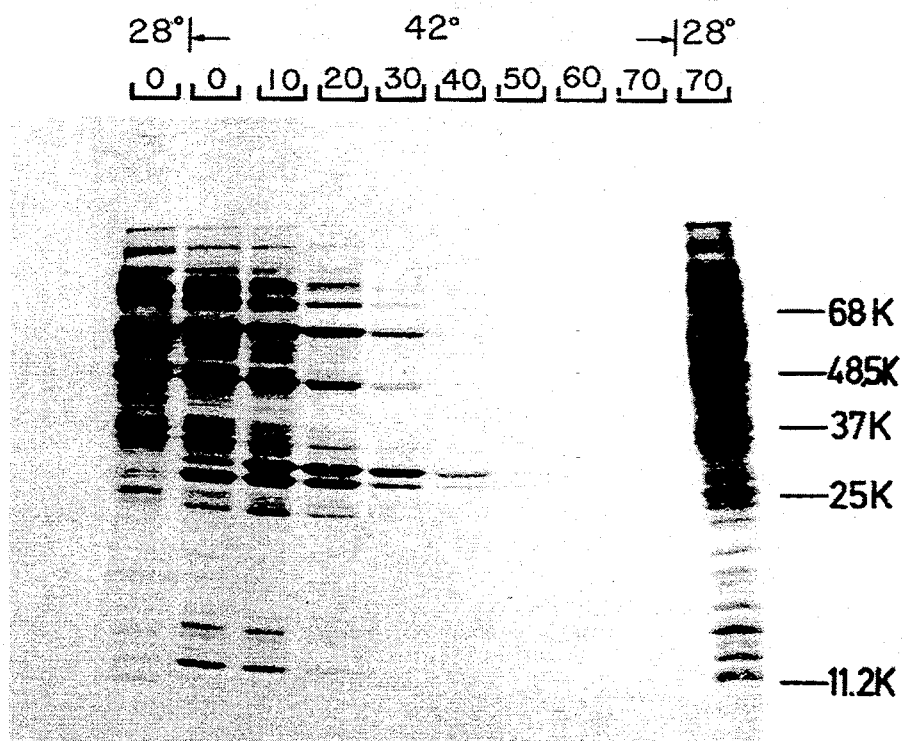
E.coli M5219 (pPLa23)
FIG. 8B

FIG. 9A
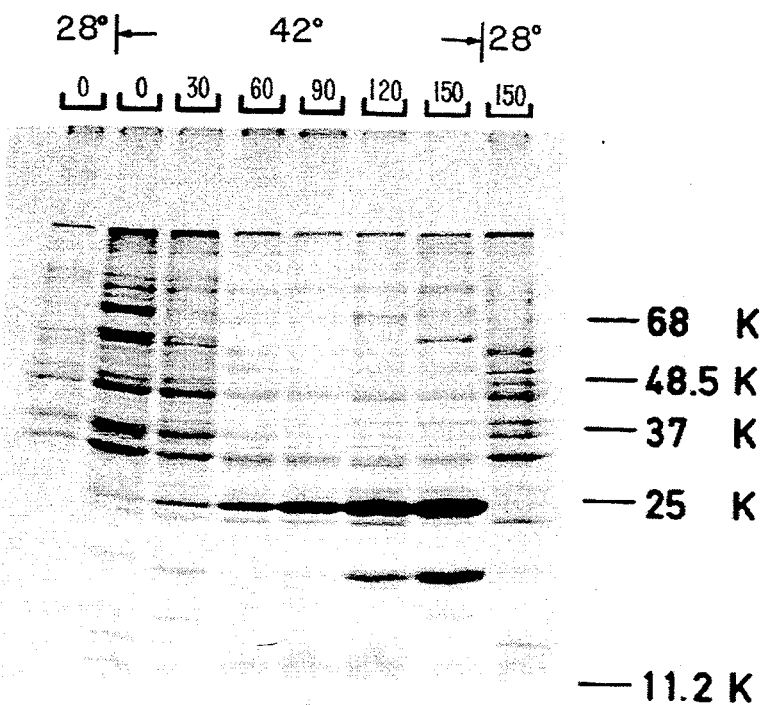
E.coli K12 ΔHI (pPLa23trpA₁)
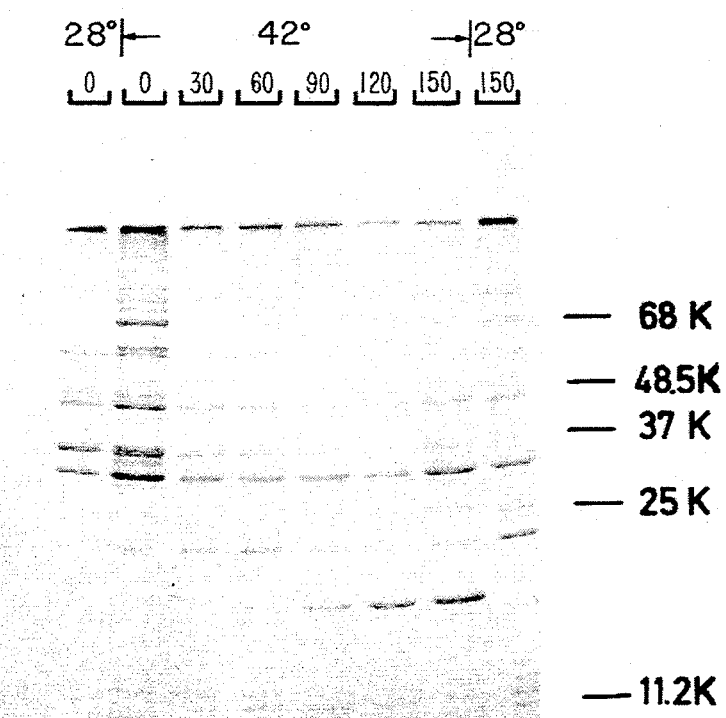
E.coli K12 ΔHI (pPLatrpA₂)
FIG. 9B E.coli K12 ΔHI (pPLa2311R₁)

E.coli K12ΔHI (pPLc28SVt5-37-9)

VECTORS AND METHODS FOR MAKING SUCH VECTORS AND FOR EXPRESSING CLONED GENES

This is a continuation of application Ser. No. 387,505, filed Jul. 28, 1989, now abandoned entitled Vectors And Methods For Making Such Vectors And For Expressing Cloned Genes, which is a division of application Ser. No. 921,803, filed Oct. 20, 1986, (now U.S. Pat. No. 4,874,702), which is a continuation of application Ser. No. 250,608, filed Apr. 3, 1982, (now abandoned).

TECHNICAL FIELD OF INVENTION

This invention relates to improved vectors and methods for making such vectors and for expressing cloned genes. The vectors and methods disclosed herein are characterized by the improved expression of cloned genes particularly those of eukaryotic origin in prokaryotic hosts. As will be appreciated from the disclosure to follow, these vectors and methods may be used to improve the production of various polypeptides, proteins and amino acids in host cells.

BACKGROUND ART

The level of production of a protein in a host cell is governed by three major factors: the number of copies of its gene within the cell, the efficiency with which those gene copies are transcribed and the efficiency with which the resultant messenger RNA ("mRNA") is translated. Efficiency of transcription and translation (which together comprise expression) is in turn dependent upon the nucleotide sequences which are normally situated ahead of the desired coding sequence. These nucleotide sequences or expression control sequences define, inter alia, the location at which RNA polymerase interacts (the promoter sequence) to initiate transcription and at which ribosomes bind and interact with the mRNA (the product of transcription) to initiate translation.

Not all such expression control sequences function with equal efficiency. It is thus often of advantage to separate the specific coding sequence for a desired protein from its adjacent nucleotide sequences and to fuse it instead to other expression control sequences so as to favor higher levels of expression. This having been achieved, the newly engineered DNA fragment may be inserted into a higher copy number plasmid or a bacteriophage derivative in order to increase the number of gene copies within the cell and thereby further to improve the yield of expressed protein.

Because over-production of even normally non-toxic gene products may be harmful to host cells and lead to decreased stability of particular host-vector systems, a good expression control sequence, in addition to improving the efficiency of transcription and translation of cloned genes, should also be controllable so as to modulate expression during bacterial growth. For example, the preferred expression control sequences are ones that may be switched off to enable the host cells to propagate without excessive build-up of gene products and then to be switched on to promote the expression of large amounts of the desired protein products.

Several expression control sequences, which satisfy some of the criteria set forth above, have been employed to improve the expression of proteins and polypeptides in bacterial hosts. These include, for example, the operator, promoter and ribosome binding and interaction sequences of the lactose operon of E. coli (e.g., K. Itakura et al., "Expression In Escherichia coli Of A Chemically Synthesized Gene For The Hormone Somatostatin", Science, 198, pp. 1056–63 (1977); D.V. Goeddel et al., "Expression In Escherichia coli Of Chemically Synthesized Genes For Human Insulin", Proc. Natl. Acad. Sci. USA, 76, pp 106–10 (1979)), the corresponding sequences of the tryptophan synthetase system of E. coli (J.S. Emtage et al., "Influenza Antigenic Determinants Are Expressed From Haemagglutinin Genes Cloned In Escherichia coli", Nature, 283, pp. 171–74 (1980); J.A. Martial et al., "Human Growth Hormone: Complementary DNA Cloning And Expression In Bacteria", Science, 205, pp. 602–06 (1979)) and the major operator and promoter regions of phage λ (H. Bernard et al., "Construction Of Plasmid Cloning Vehicles That Promote Gene Expression From The Bacteriophage Lambda $P_L$ Promoter", Gene, 5, pp. 59–76 (1979)). This invention relates to the last of these expression control sequences.

Bacteriophage λ contains three major promoters — $P_L$, $P_R$ and $P'_R$. A repressor protein, the product of phage gene cI, is known to control the activity of promoters $P_L$ and $P_R$. The repressor binds to the respective operator regions —$O_L$ and $O_R$— of these promoters and blocks initiation of transcription from the corresponding promoter. Moreover, due to its autoregulating mode of synthesis (M. Ptashne et al., "Autoregulation And Function Of A Repressor In Bacteriophage λ", Science, 194, pp. 156–61 (1976)), one copy of the cI gene on the chromosome of a lysogenic strain is able to repress fully the $P_L$ or $P_R$ promoters present in a multi-copy plasmid (infra). It should be noted that in systems involving the lac promoter repression of the promoter under non-induced conditions is only partial (K. Itakura et al., supra; D.V. Goeddel et al., supra).

The control exerted by the repressor over promoters $P_L$ and $P_R$ may be altered by modification of the repressor protein or its gene. For example, one mutation is known where the repressor protein is temperature sensitive. When that mutation is employed, the promoters may be activated or inactivated by varying the temperature of the culture and hence the stability of the repressor.

Bacteriophage A also contains genes N and cro. The N gene is under $P_L$ control. The product of the N gene is known to act as an anti-terminator in bacteriophage λ. Anti-termination is advantageous in overriding transcript termination or slow-down caused by the presence of termination sequences, termination-like sequences or transcription slow-down sequences in the particular DNA sequences that are to be transcribed. Furthermore, polarity effects, introduced by the presence of nonsense codons in the promoter transcript, may be relieved by the N gene product (N. Franklin & C. Yanofsky, "The N Protein Of λ: Evidence Bearing On Transcription Termination, Polarity And The Alteration Of E. coli RNA Polymerase", in RNA Polymerase (Cold Spring Harbor Laboratory) pp. 693–706 (1976)).

The product of the cro gene transcribed from the $P_R$ promoter is known to be a secondary repressor for both promoters $P_L$ and $P_R$ (J. Pero, "Deletion Mapping Of The Site Of The tof Gene Product", in The Bacteriophage λ, (Cold Spring Harbor Laboratory), pp. 549–608 (1971); H. Echols, "Role Of The cro Gene In Bacteriophage A Development", J. Mol. Biol., 80, pp. 203–16 (1973); A. Johnson et al., "Mechanism Of Action Of The cro Protein Of Bacteriophage λ", Proc. Natl.

Acad. Sci. USA, 75, pp. 1783–87 (1978)). Because the cro gene product is co-produced along with the desired products of the host-vector combination, the cro gene product's effect on expression from the $P_L$ or $P_R$ promoters tends to increase with time. Therefore, in any system where continued high levels of expression are desired, deletion or inactivation of the cro gene is necessary.

The effectiveness of the $P_L$ promoter for expression of cloned genes has been demonstrated by incorporating the tryptophan (trp) operon of E. coli into phage λ. (N. Franklin, "Altered Reading Of Genetic Signals Fumed To The N Operon Of Bacteriophage λ: Genetic Evidence For Modification Of Polymerase By The Protein Product Of The N Gene", J. Mol. Biol., 89, pp. 33–48 (1979); A. Hopkins et al., "Characterization Of λ trp—Transducing Bacteriophages Made In Vitro", J. Mol. Biol., 107, pp. 549–69 (1976)). In this modified phage, the trp genes can be transcribed either from their own promoter or from the $P_L$ promoter. $P_L$ mediated expression was found to be 3–4 times higher than the levels obtained from the homologous trp promoter.

The effect of repressor on $P_L$ mediated expression was also demonstrated in this modified phage. For example, in the absence of repressor, $P_L$ controlled expression of antranilate synthetase (the first enzyme in the trp operon) was 11 times greater than that observed for the enzyme under trp promotion in the absence of trp repressor (J. Davison et al., "Quantitative Aspects Of Gene Expression In A λ trp Fusion Operon", Molec. gen. Genet., 130, pp. 9–20 (1974)). Yet, in the presence of an active cI gene, $P_L$ mediated expression of the enzyme was reduced at least 900-fold. These studies also demonstrated that continued high level of $P_L$ mediated transcription was only possible if the cro gene was not functional in the host.

The problem is that although the above-described λ trp phages demonstrate the utility of the $P_L$ promoter for the expression of inserted genes, the use of such phages is somewhat restricted by difficulties in construction and stable propagation of cro⁻ acceptor phages. Without such phages, the observed high levels of expression soon drop off as the level of the co-produced cro gene product increases and represses transcription from the $P_L$ promoter.

While the disadvantage of λ phages has been somewhat overcome by cloning the λ control elements on an autonomously replicating plasmid such as Col EI or its derivatives (J. Hedgpeth al., "Lambda Phage Promoter Used To Enhance Expression Of A Plasmid-Cloned Gene", Molec. gen. Genet., 163, pp. 197–203 (1978)) or by constructing smaller plasmids that incorporate only the λ $P_L$ system (H. Bernard et al., supra), these latter vectors are disadvantaged by the distance between the sites available for insertion of cloned genes and the $P_L$ promoter. For example, in the vectors described by H. Bernard et al., supra, the distance between the sites of gene insertion and the $P_L$ promoter on the vector range from about 300 to about 8600 bases. Moreover, the more commonly used EcoRI and BamHI insertion sites in Bernard et al.'s vectors are not closer than 600 to 1000 bases, respectively, to the $P_L$ promoter. In addition, the effect of the N gene product on transcription of the desired DNA sequences cannot be readily assessed in Bernard et al.'s vectors because the N gene product is encoded on the plasmid itself and is not of chromosomal origin. Finally, in addition to there being no direct evidence that Bernard's vectors afford higher levels of protein expression, there is no teaching in Bernard that his vectors are usefully employed in the expression of eukaryotic gene products in prokaryotic hosts.

DISCLOSURE OF THE INVENTION

The present invention solves the problems referred to by providing an improved vector and method for making such vectors and for expressing cloned genes in host cells.

More specifically, we provide in accordance with this invention a vector comprising at least one DNA sequence comprising at least one promoter and operator derived from bacteriophage, characterized by at least one endonuclease recognition site located less than about 300 base pairs from that portion of said DNA sequence comprising said promoter and operator.

The major promoters of phage λ in the vectors of this invention promote the transcription of DNA sequences inserted into those vectors. The methods and vectors of this invention are further characterized by the presence of numerous appropriate recognition sites for the insertion of desired DNA sequences into the vectors near the chosen promoter. Preferably, the distance between the chosen promoter and the recognition sites is less than about 300 base pairs and more preferably less than about 150 base pairs. The preferred vectors of this invention are also those in which active N genes and active cro genes are absent. Therefore, by choice of appropriate host, i.e. one containing or lacking an active chromosomal N gene, any of the vectors of the invention may be employed for expression of DNA sequences in the presence or in the absence of the N gene product.

As will be appreciated from the description to follow, the vectors and methods of this invention permit the construction of host-vector combinations that enable improved expression of prokaryotic and eukaryotic products in host cells.

BRIEF DESCRIPTION OF THE DRAWINGS

FIG. 6 displays the nucleotide sequence of the $O_LP_L$ region of pPLa2311.

FIGS. 8A and 8B are autoradiographs monitoring protein synthesis at 28° C. and 42° C. in E. coli K12ΔHI (pPLa23) and E. coli M5219 (pPLa23).

FIGS. 9A and 9B are autoradiographs monitoring protein synthesis at 28° C. and 42° C. in E. coli K12ΔHI (pPLa23trPA₁) and E. coli K12ΔHI (pPLa23trpA₂).

BEST MODE OF CARRYING OUT THE INVENTION

Figure 1:
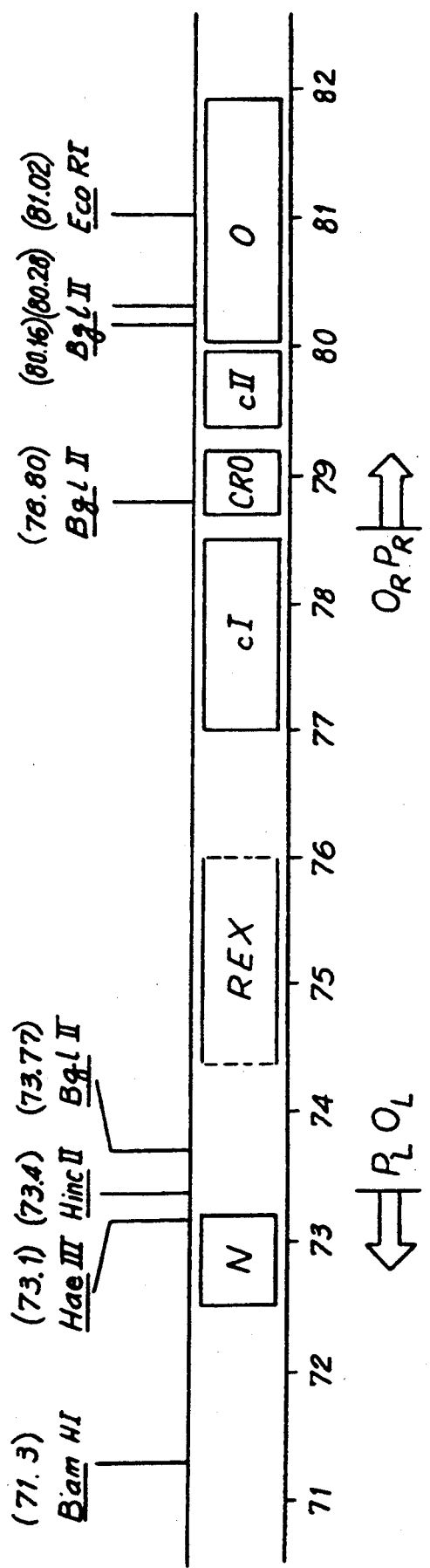
FIG. 1 is a schematic outline of a region of phage λ trp 44 cIAt₂ cro⁻. Not all restriction sites have been depicted. The distances are mapped in λ units as described by E. Szybalski & W. Szybalski, "A Comprehensive Molecular Map Of Bacteriophage Lambda", Gene, 7, pp. 217–70 (1979).

In order that the invention herein described may be more fully understood, the following detailed description is set forth.

In the description the following terms are employed:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes, through its template or messenger RNA ("mRNA"), an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal.

polypeptide—A linear array of amino acids connected one to the other by peptide bonds between the α-amino and carboxy groups of adjacent amino acids.

Structural Gene—A DNA sequence which encodes through its mRNA a sequence of amino acids characteristic of a specific polypeptide.

Transcription—The process of producing mRNA from a structural gene.

Translation—The process of producing a polypeptide from mRNA.

Expression—The process undergone by a structural gene to produce a polypeptide. It is a combination of transcription and translation.

Plasmid—A nonchromosomal, double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance (Tet$^R$) transforms a cell previously sensitive to tetracycline into one which is resistant to it. A host cell transformed by a plasmid or vector is called a "transformant".

Phage or Bacteriophage—Bacterial virus many of which consist of DNA sequences encapsidated in a protein envelope or coat ("capsid").

Cloning Vehicle or Vector—A plasmid, phage DNA or other DNA sequence which is able to replicate in a host cell, characterized by one or a small number of endonuclease recognition or restriction sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance.

Cloning—The process of obtaining a population of organisms or DNA sequences derived from one such organism or sequence by asexual reproduction.

Recombinant DNA Molecule or Hybrid DNA—A molecule consisting of segments of non contiguous DNA which have been joined end-to-end.

Expression Control Sequence—A sequence of nucleotides that controls and regulates expression of genes when operatively linked to those genes.

THE HOST CELLS OF THIS INVENTION

Any of a large number of available host cells may be used in the host-vector combinations of this invention. The selection of a particular host is dependent upon a number of factors recognized by the art. These include, for example, compatibility with the chosen vector, toxicity of proteins encoded by the hybrid plasmid, ease of recovery of the desired protein, expression characteristics, bio-safety and costs. A balance of these factors must be struck with the understanding that not all hosts may be equally effective for expression of a particular recombinant DNA molecule. Within these general guidelines, useful hosts may include strains of *E. coli*, *Pseudomonas*, *Bacillus subtilis*, *Bacillus stearothermophilus*, and other bacilli, yeasts and other fungi, animal or plant hosts such as animal (including human) or plant cells in culture or other hosts.

The preferred host cells of this invention are *E. coli* strains K12 cI$_{ts}$ΔHI (K12 M72 lac$_{am}$ ΔtrpEA2 Sm$^R$ (λCI857 N$_{am}$7N$_{am}$53ΔHI bio⁻)) ("K12ΔHI") (H. Bernard et. al., supra) and M5219 (K12 M72 lac$_{am}$ trp$_{am}$ Sm$^R$ (λCI857 ΔHI bio252)) ("M5219") (H. Greer, "The kil Gene Of Bacteriophage λ", *Virology*, 66, pp. 589–604 (1975)) or any other strain harboring either a chromosomally- or plasmid-coded cI857 gene (or its equivalent).

Both strains harbor a defective, non-excisable λ prophage carrying a mutant cI gene. The mutant gene codes for a temperature-sensitive repressor, thus allowing transcription from the P$_L$ promoter to be activated by adjusting the temperature—at 28° C. the repressor is active and transcription from the P$_L$ promoter is repressed but at 42° C. the repressor is inactivated and transcription from the P$_L$ promoter is switched on.

The ΔHI deletion of the prophage removes part of the cr$_0$ gene and all other genes further to the right of cro in the prophage (M. Castellazzi et al., "Isolation And Characterization Of Deletions In Bacteriophage λ Residing As Prophage In *E. coli* K12", *Mol. gen. Genet.*, 117, pp. 211–18 (1972)).

Strain M5219, in addition, contains a bio252 deletion which removes all genes to the left of cIII, including kil in the prophage. Moreover, upon temperature induction strain M5219 expresses a functional N-gene product from a chromosomal N gene. Strain K12ΔHI, on the other hand, has two amber mutations in N rendering it functionally N-negative.

Therefore, the two strains allow experimental switching on or off of expression from the $P_L$ promoter. Furthermore, a choice of K12ΔHI or M5219 allows $P_L$ mediated transcription to proceed in the absence or presence of the N-gene product. And, because neither E. coli K12ΔHI or E. coli M5219 expresses a functional cro gene product, secondary repression of $P_L$ mediated expression is avoided in them.

CONSTRUCTION OF SEVERAL EMBODIMENTS OF VECTORS OF THIS INVENTION

Although there are several well recognized sources for the phage λ promoters, for the purpose of the following illustrative examples of the construction of vectors in accordance with this invention, phage λ trp 44 cIAt$_2$ cro⁻ was chosen as the source of phage λ promoters.

The generation of phage λ trp 44 cIAt$_2$ cro⁻ is described by N. Franklin, "The N Operon of Lambda: Extent And Regulation As Observed In Fusions To The Tryptophan Operon Of *Escherichia Coli*", in *The Bacteriophage* λ (Cold Spring Harbor Laboratories), pp. 621-38 (1971). The At$_2$ mutation in the cI gene renders the repressor thermolabile (M. Lieb, "Studies Of Heat-Inducible Lambda Bacteriophages. I. Order Of Genetic Sites And Properties Of Mutant Prophages", J. Mol Biol., 16, pp. 149-63 (1966)). The cro⁻ mutation prevents secondary repression of $P_L$ function. Of course, it should be understood that although less preferable for long term expression cro⁺ phages might be employed in the vectors of this invention. The phage also carries a functional N gene and active $P_L$ promoter. The phage yields 3- to 4-fold higher levels of trp enzyme expression than that yielded by the homologous trp promoter itself (N. Franklin, supra).

λ trp 44 cIAt$_2$ cro⁻ DNA was prepared from this phage by phenol extraction from CsCl-purified phage particles. The structure of the $P_L O_L$ region of this phage is shown in FIG. 1.

The $P_L$ promoter and adjacent operators ($O_L$) together with the start of the N gene sequence is defined within a stretch of DNA, approximately one hundred base pairs long, located at about 73.4% on the λ map (FIG. 1) (T. Maniatis et al., "Recognition Sequences Of Repressor And Polymerase In Operators Of Bacteriophage λ", Cell, 5, pp. 109-13 (1975); J. Dahlberg & F. Blattner, "Sequence Of Promoter-Operator Proximal Region Of The Major Leftward RNA Of Bacteriophage λ", Nucleic Acids Res., 2, pp 1441-58 (1975)). Likewise, the $P_R$ promoter and adjacent operator ($O_R$) together with the start of the cro gene sequence is defined within a stretch of DNA located at about 76.6% on the λ map (FIG. 1) (T. Maniatis et al., supra).

Any of several means for isolating these regions from phage λ DNA may be employed to prepare clones containing the desired promoter sequences. For example, various combinations of restriction enzymes may be used to cleave the desired regions from the phage λ DNA (FIG. 1). These fragments may then be used directly to prepare clones or the fragments may be further treated to trim or to extend them by methods known in the art before cloning.

After preparation of the appropriate DNA fragment it may be inserted into any of several cloning vehicles or vectors. For example, useful cloning vehicles may consist of segments of chromosomal, non-chromosomal and synthetic DNA sequences such as various known derivatives of SV40 and known bacterial plasmids, e.g., plasmids from E. coli including Col El, pCR1, pBR322, pMB9 and their derivatives, wider host range plasmids, e.g., RP4, phage DNAs, e.g., the numerous derivatives of phage λ, other DNA phages, Filamenteous single stranded DNA phages, e.g. M13, and vectors derived from combinations of plasmid and phage DNAs or yeast plasmids such as the 2 μ plasmid or derivatives thereof.

Furthermore, within each specific cloning vehicle, various sites may be employed for insertion of the phage λ DNA fragment. These sites are usually designated by the restriction endonuclease which cuts them. For example, in pBR322 there are various restriction sites available for DNA fragment insertion (F. Bolivar et al., "Construction And Characterization Of New Cloning Vehicles II. A Multi-Purpose Cloning System", Gene, 2, pp. 95-113 (1977); J. G. Sutcliffe, "pBR322 Restriction Map Derived From the DNA Sequence: Accurate DNA Size Markers Up To 4361 Nucleotide Pairs Long", *Nucleic Acids Res.*, 5, pp. 2721-28 (1978)). See also FIGS. 2 and 4. It is, of course, to be understood that a cloning vehicle useful in this invention need not have a restriction site for insertion of the phage λ DNA fragment. Instead, the vehicle could be joined to the fragment by alternative means to produce the desired vector in accordance with the invention.

A. Vectors According To This Invention Containing The $P_L$ Promoter In The Anti-Clockwise Orientation with Respect To The Origin Of Replication
  1. pPLa23

Figure 2:
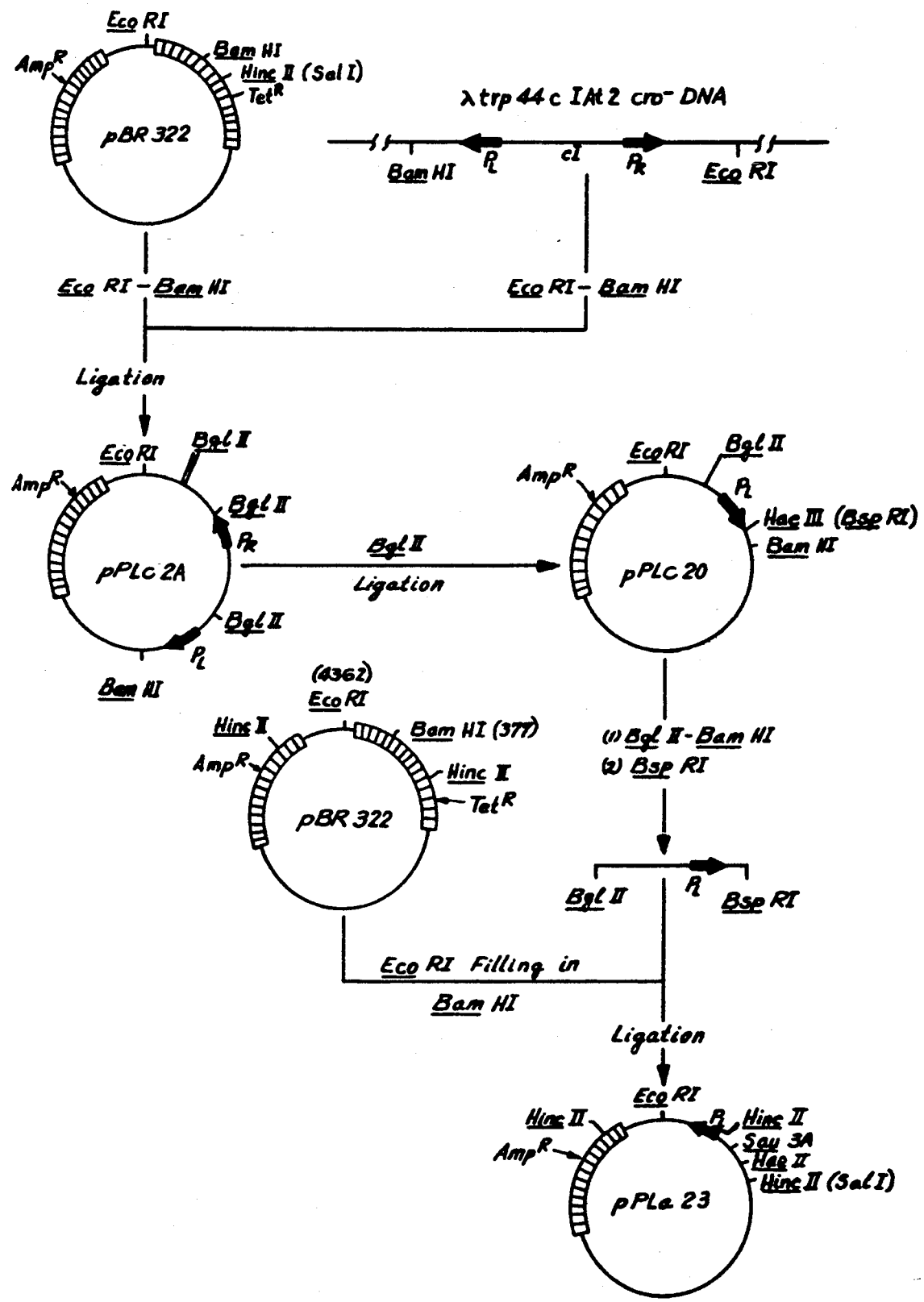
FIG. 2 is a schematic outline of the construction of vectors in accordance with this invention—pPLa2, pPlc2A and pPLc2O.

Referring now to FIG. 2, one improved vector of this invention pPLa23 was prepared in a sequence of steps. These are depicted in FIG. 2 and more fully described below.

(a) Intermediate Plasmid pPLa2

The λ trp 44 cIAt$_2$ cro⁻ DNA isolated above was digested with BamHI and EcoRI to excise a fragment extending from about 71.3% to 81.02% on the A map (FIGS. 1 and 2). In like manner, pBR322 was digested with BamHI and EcoRI and the phage A DNA fragment inserted in place of the excised EcoRI-BamHI pBR322 fragment (FIG. 2).

The resultant vector was designated pPLa2A, the serving to indicate the anticlockwise orientation of the $P_L$ promoter with respect to the origin of replication. The λ information on this molecule extends from the BamHI site of the phage (71.3% λ) to the EcoRI site (81.02% λ) and includes the gene N, the $O_L P_L$ region, genes rex and cI (mutant), the $O_R P_R$ region, genes cro (mutant) and cII and part of gene O (FIGS. 1 and 2).

E. coli C600 (CaCl$_2$ competent) was transformed with the above prepared pPLa2A Under appropriate conditions and containment. Transformants were selected at 34° C. on LB plates seeded with 10$^9$ pfu of phage λ$_{clear}$ mutant (M. Lieb, supra) and also containing 100 μg/ml carbenicillin. The chosen λ DNA fragment includes the cIAt$_2$ gene and therefore transformants containing this fragment will be resistant to phage λ$_{clear}$ mutant at 34° C. In addition, the chosen pBR322 fragment includes the gene for ampicillin resistance so that hosts transformed with plasmids having that gene intact will grow in cultures containing that antibiotic to the exclusion of those hosts not so transformed.

Twenty transformants were selected and cultures grown at 34° C. in LB medium containing 100 μg/ml carbenicillin and $10^{-2}$M $MgCl_2$. To insure that the transformants were true transformants harboring a cI gene and not rare bacteria unable to adsorb λ phage, aliquots of the cultures were infected with either $\lambda_{clear}$ or $\lambda_{vir}$ (F. Jacob & E. Wollman, "Etude Genetique d'un Bacteriophage Tempere d'*Escherichia Coli.* I. Le Systeme Genetique du Bacteriophage λ", Ann. Inst. Pasteur, 87, pp. 653–90 (1954)). All twenty transformants displayed resistance to $\lambda_{clear}$ and sensitivity to $\lambda_{vir}$.

Form I DNA from one of these twenty transformants was isolated using standard procedures, restricted with EcoRI and BamHI and sized against standard markers. The DNA displayed two bands corresponding to the expected sizes. of the pBR322 fragment and the phage λ fragment.

(b) Intermediate Plasmid pPLa20 —Elimination of BglII Fragments From pPLc2A

The A region of pPLc2A includes four BglII sites located at 73.77, 78.80, 80.16 and 80.28% λ (FIGS. 1 and 2) (V. Pirotta, "Two Restriction Endonucleases From Bacillus Globigi;", *Nucleic Acids Res.*, 3, pp. 1747–60 (1976); H. Szybalski & W. Szybalski, "A Comprehensive Molecular Map of Bacteriophage λ", Gene, 7, pp. 217–70 (1979)).

To eliminate the BglII fragments between 73.77% λ and 80.28% λ, pPLc2A DNA was digested with BglII, religated at a DNA concentration of less than 1 μg/ml and transformed into *E. coli* W6 ($\lambda_{rex}$) ($CaCl_2$ competent) having a chromosomal λ repressor cI so as to silence $P_L$ dependent transcription (FIG. 2). Carbenicillin resistant clones were selected by growth in L-broth containing 100 μg/ml carbenicillin and screened for loss of $\lambda_{rex}$ function using a $T_4$ rII 638 mutant. The $\lambda_{rex}$ function prevents growth of the $T_4$ rII 638 mutant (B. Howard, "Phage λ Mutants Deficient In rII Exclusion", *Science* 158, pp. 1588–89 (1967)). Therefore, the failure of these BglII restricted transformants to prevent the growth of the $T_4$ rII 638 mutant as compared with the lack of growth of the mutant in hosts transformed with pPLc2A demonstrated that the rex function had been eliminated from the pPLc2A recombinant DNA molecule by the BglII deletion.

Restriction analysis of the recombinant DNA molecules of these BglII restricted transformants revealed the presence of a single BglII site. Moreover, digestion with EcoRI and BamHI produced two fragments—one corresponding to the expected pBR322 fragment and the other to the expected size (1900 base pairs) of the phage λ DNA fragment after elimination of that portion between BglII sites 73.77% λ and 80.28% λ. This modified plasmid was designated pPLc20. Its A DNA insert extends from the BamHI site (71.3%) to the BglII site (73.77%) and from the BglII site (80.28%) to the EcoRI site (81.02%). It includes gene N, the $O_LP_L$ region and part of gene O (FIG. 1).

While the remainder of this example of the construction of embodiments of vectors of this invention focuses on the $P_L$ promoter—the $P_R$ promoter having been eliminated from pPLc2A with the BglII-BglII fragment—it should be understood that similar manipulations could have been employed to eliminate the $P_L$ promoter from pPlc2A and to construct a vector retaining the $P_R$ promoter. In addition, vectors within this invention could be constructed by similar means having both the $P_L$ and $P_R$ promoters present such that the two promoters act in concert or in opposition to mediate the expression of inserted DNA sequences.

(c) pPLa23—Introduction Of An EcoRI Site At A Short Distance Downstream From $P_L$ The BglII-BamHI fragment present on pPLc20 contains a single HaeIII site [73.1% λ, FIG. 1] located about 150 nucleotides downstream from $P_L$ (B. Allet and R. Solem "Separation And Analysis Of Promoter Sites In Bacteriophage A DNA By Specific Endonucleases" *J. Mol. Biol.* 85, 475–84 (1975)). This site can be converted into an EcoRI site by flush-end ligation of an open HaeIII end to an open EcoRI end previously flush-ended by extending the recessed 3′-end with DNA polymerase I in the presence of deoxyribonucleoside triphosphates (K. Backman et al. "Construction Of Plasmids Carrying The cI Gene Of Bacteriophage λ", *Proc. Natl. Acad. Sci. U.S.A.*, 73, pp. 4174–78 (1976)). Details of the procedure are described below and illustrated in FIG. 2.

Six pmol of pBR322 was digested with EcoRI. After heat-killing the enzyme, the DNA was precipitated and dissolved in 250 μl of a buffer containing 50 mM Tris-HCl (pH 7.8), 5 mM$MgCl_2$, 1 mM β-mercaptoethanol, 2 μM of each of the four deoxyribonucleoside triphosphates (with α-$^{32}$P-dATP (345 Ci $^{32}$P/mmol)) and 50 μg BSA/ml. Six units of DNA polymerase I from *E. coli* (Worthington) were added and the mixture was incubated at 16° C. for 90 min. This process resulted in the flush-ending of the open 3′ EcoRI site in the linearized pBR322.

After heat-inactivation of the enzyme, the mixture was adjusted to 50 mM NaCl, 7 mM β-mercaptoethanol and the DNA digested with BamHI. The fragments were separated by electrophoresis on a 1.4% agarose gel and monitored by autoradiography. A gel slice containing the larger of the two fragments—pBR322 containing an open BamHI site and a flushed ended EcoRI site—was cut out and frozen at −90° C. This piece of agarose was then centrifuged (SS34 rotor (Sorvall)) for 20 min at 20,000 rpm. The expelled supernatant was removed and the freezing and centrifugation steps repeated two additional times. Under these conditions about 30% of the DNA contained within the agarose slice is expelled into the supernatant. The expelled DNA was precipitated from the combined supernatants and dissolved in 10 μl of 10 mM Tris-HCl (pH 7.4), 50 mM NaCl, 7 mM β-mercaptoethanol.

Two pmol of pPLc20 was digested with BglII and BamHI and the fragments separated on agarose gel. The smaller fragment (BglII-BamHI) was eluted from the gel as described above and digested with BspRI, an isoschizomer of HaeIII (A. Kiss et al. "A New Sequence-Specific Endonuclease (Bsp) From *Bacillus Sphaericus*", Gene, 1, pp. 323–29 (1977)) to produce a mixture of BamHI-BspRI and BspRI-BglII fragments, the latter carrying the $P_L$ promoter. The enzymes BglII and BamHI make identical open ends such that an open BglII end can be ligated to an opened BamHI end and vice versa. Moreover, the result of either ligation is no longer a substrate for BglII or BamHI but is recognized by the enzyme Sau3A1 (MboI) (V. Pirotta, supra).

Two pmol of the aforementioned pBR322-EcoRI-BamHI larger fragment was ligated to 0.8 pmol of the mixture of BamHI-BspRI and BspRI-BglII fragments. Following ligation (the open BamHI site on the pBR322 fragment is available for ligation to either the open BglII or BamHI sites of the pPLc20 fragments and the flush-ended EcoRI site of the pBR322 fragment is available for ligation to the BspRI (HaeIII) sites of the pPLc20 fragments), the mixture was digested with BamHI to eliminate those recombinant molecules comprising the unwanted BamHI-BspRI fragment inserted in the pBR322 vector. The resulting mixture was transformed into E. coli M5219 and transformants selected for resistance to carbenicillin. A total of 23 transformants was obtained. All of these transformants were sensitive to tetracycline (also carried by pBR322) because the BamHI restriction of pBR322 rendered the gene coding for Tet$^R$ no longer intact in the modified plasmid (FIG. 2).

The continued presence in these clones of the $P_L$-carrying BspRI-BglII fragment was checked by digesting the DNA with HincII. Since pBR322 contains two HincII sites (J. Sutcliffe, supra) and the expected λ $P_L$ fragment contains a single HincII site (73.4% λ, FIG. 1) (B. Allet and R. Solem, supra) correctly constructed recombinant DNA molecules should contain three HincII sites. Of the 23 transformants obtained, five contained the three predicted HincII sites. Three of these had a unique EcoRI site indicating that in those clones the correct junction between the BspRI (HaeIII) site of the pPLc20 fragment and the flush-ended EcoRI site of the pBR322 fragment had been made. These three clones also lacked a BamHI site as predicted by the expected ligation of the BglII end of the pPLc20 fragment to the BamHI end of the pBR322 fragment. One of these clones was chosen for further work and was designated pPLa23 (FIG. 2).

pPLa23 consists of a pBR322 fragment extending from the BamHI site (base pair 377 of pBR322) to the EcoRI site (base pair 4362 of pBR322) (J. Sutcliffe, supra) (FIG. 2). The remaining part of pBR322 has been replaced in pPLa23 by the fragment of λ trp 44 cIAt$_2$ cro⁻DNA located between the HaeIII site at 73.3% λ (now a reconstructed EcoRI site) and the BglII site at 73.77% λ (now an Sau3A site) (FIG. 2). The size of this fragment was estimated by agarose gel electrophoresis to be about 300 base pairs. Within this fragment are contained the $O_LP_L$ region and the first 115 nucleotides of the N gene transcript (J. Dahlberg & F. Blattner, supra). The direction of transcription of the $P_L$ promoter is from the BglII site towards the HaeIII site and runs in the same sense as transcription from the β-lactamase promoter of pBR322 (J. Dahlberg & F. Blattner, supra; J. Sutcliffe, supra).

Figure 3:
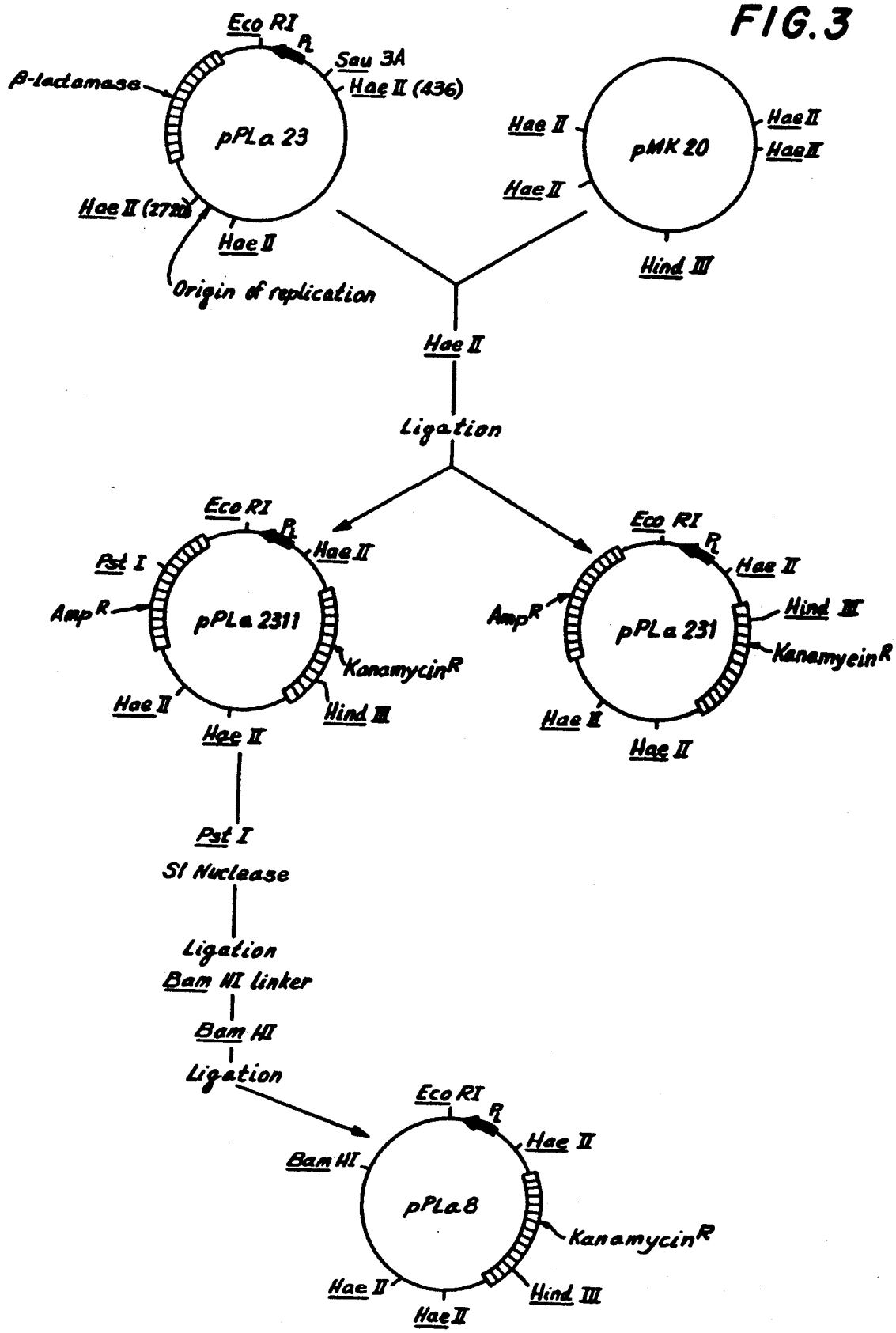
FIG. 3 is a schematic outline of the construction of vectors in accordance with this invention—pPLa2311, pPLa231 and pPLa8.

Two features of the plasmid are of special interest: 1) The regions coding for the $P_L$ promoter and for the β-lactamase gene are present on a single HaeII fragment, delineated by the HaeII sites at base pair 2720 and 436 of pBR322 (FIG. 3) (J. Sutcliffe, supra; B. Allet and R. Solem, supra; V. Pirotta, supra). 2) The origin of replication is located on a 370 base pair HaeII fragment adjacent to the β-lactamase-carrying HaeII fragment (FIG. 3). A functional origin of replication requires that the junction around the HaeII site at position 2720 be maintained (A. Oka et al. "Nucleotide Sequence Of Small Col E1 Derivatives. Structure Of The Regions Essential For Autonomous Replication And Colicin E1 Immunity", Mol. gen. Genet., 172, pp. 151–59 (1979)). These features of pPLa23 were utilized to introduce a second antibiotic resistance marker into the vector.

2. pPLa231 and pPLa2311—Introduction Of A Kanamycin Resistance Marker Into pPLa23

Referring now to FIG. 3, the steps employed to prepare other vectors of this invention from pPLa23 are depicted. These steps are more fully described below.

A HaeII fragment coding for resistance to kanamycin was obtained from plasmid pMK20 (M. Kahn et al., "Plasmid Cloning Vehicles Derived From Plasmids ColEl, F, R6K and RK2", Methods in Enzymology, 68, pp. 268–80 (1979)). The origin of replication on plasmid pMK20 is largely contained within a 359 base pair HaeII fragment. However, the origin also spans the junction between this fragment and. an adjacent HaeII fragment (M. Kahn et al., supra). The nucleotide sequence around this HaeII site is identical to the sequence found in pBR322 around the HaeII site at position 2720 (A. Oka et al., supra; J. Sutcliffe, supra).

A mixture of pPLa23 and pMK20 was digested to completion with HaeII, religated and transformed into E. coli M5219 (CaCl$_2$ competent) (FIG. 3). Correctly transformed colonies were selected on the basis of their resistance to carbencillin and kanamycin, because only clones containing the β-lactamase gene from pBR322 and the kanamycin gene from pMK20 will display dual antibiotic resistance. Twelve dual resistant transformants were selected. Plasmid DNA was isolated from these transformants, as before, and analyzed by HaeII restriction and fragment sizing on a 6% acrylamide gel. Five of these clones had only three HaeII fragments—an HaeII fragment corresponding to the HaeII fragment of pPLa23 which carries the $P_L$ promoter and β-lactamase gene, an HaeII fragment corresponding to the HaeII fragment of pMK20 carrying the gene for kanamycin resistance and a small HaeII fragment also derived from pMK20 and required for plasmid replication (FIG. 3).

The five selected clones were further examined to determine the orientation of the kanamycin gene containing HaeII fragment from pMK20 with respect to the reconstructed EcoRI site in the HaeII fragment from pPLa23. The kanamycin gene containing HaeII fragment from pMK20 is known to contain a unique asymmetric HindIII site (M. Kahn et al., supra) (FIG. 3). Therefore, this site provides a means of determining the orientation of the fragment.

The five clones were digested with HindIII and EcoRI and the resulting fragments sized as before. Four of the five clones had the larger portion of the HindIII-cleaved kanamycin gene containing HaeII fragment from pMK20 adjacent to the origin-containing small HaeII-fragment to the reconstructed EcoRI site. One clone had the opposite orientation. These two sets of clones were arbitrarily designated pPLa231 and pPLa2311, respectively (FIG. 3).

pPLa2311 was arbitrarily selected from the above-constructed plasmids and the nucleotide sequence of the $P_L$ region determined.

Preliminary to the sequencing, two sets of restriction fragments were prepared from pPLa2311—EcoRI-HincII fragments and HincII-ECoRI-XhoI fragments (not shown in FIG. 3). In both cases pPLa2311 was digested with the first restriction enzyme and the resulting fragments labelled with $^{32}$p using T$_4$ polynucleotide Kinase (P-L Biochemicals). Then, the fragments were digested with the second restriction enzyme or pair of enzymes, in the case of EcoRI-XhoI, and the fragments separated on a 6% agarose gel. Sequencing was done conventionally using the procedures of A. Maxam & W. Gilbert, "A New Method For Sequencing DNA", Proc. Natl. Acad. Sci. USA, 74, pp. 560–64 (1977).

Figure 6:
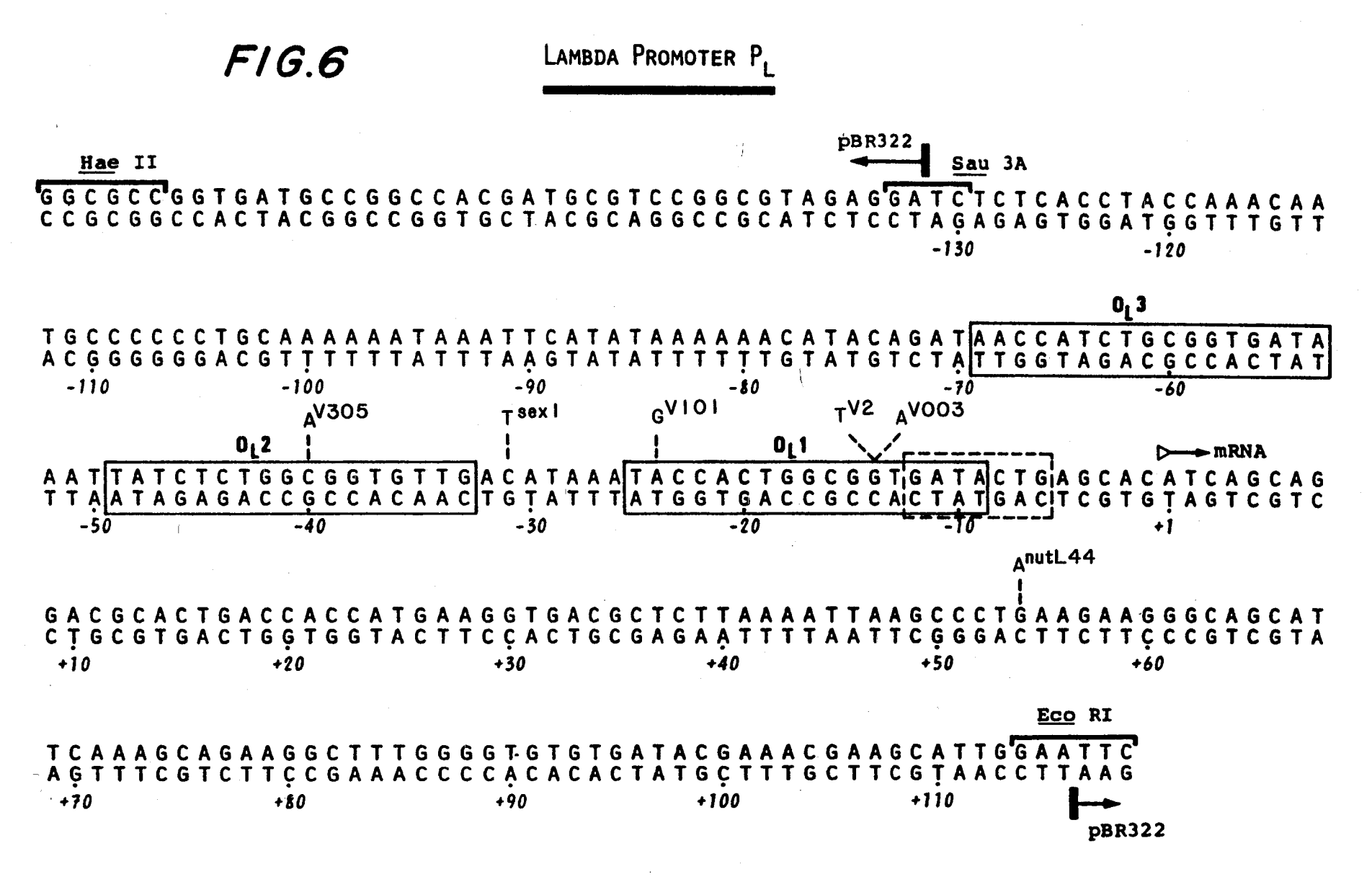

The nucleotide sequence of this region is displayed in FIG. 6. It extends from the HaeII site in pBR322 to the reconstructed EcoRI site at the junction between the λ phage fragment and pBR322. The determined sequence has the following characteristics as compared to known sequences: (1) the nucleotide sequence of the $O_L P_L$ operator-promoter region is identical to that sequence of this region in phage λ (T. Maniatis et al., supra); (2) the sequence between the HaeII site and the Sau3A site at the junction between the λ phage fragment and pBR322 is identical to that of authentic pBR322 (J. Sutcliffe, supra); (3) the sequence of the N gene transcript agrees with the sequence determined at the mRNA level by Dahlberg & Greenblatt (supra) except for a deletion of one adenosine residue at position 41 of the transcript; and (4) the sequence does not include the translational start signal of the N gene (N. Franklin & G. Bennett, "The N Protein Of Bacteriophage A, Defined By Its DNA Sequence, Is Highly Basic", Gene, 8, pp. 107-19 (1979)).

Figure 7:
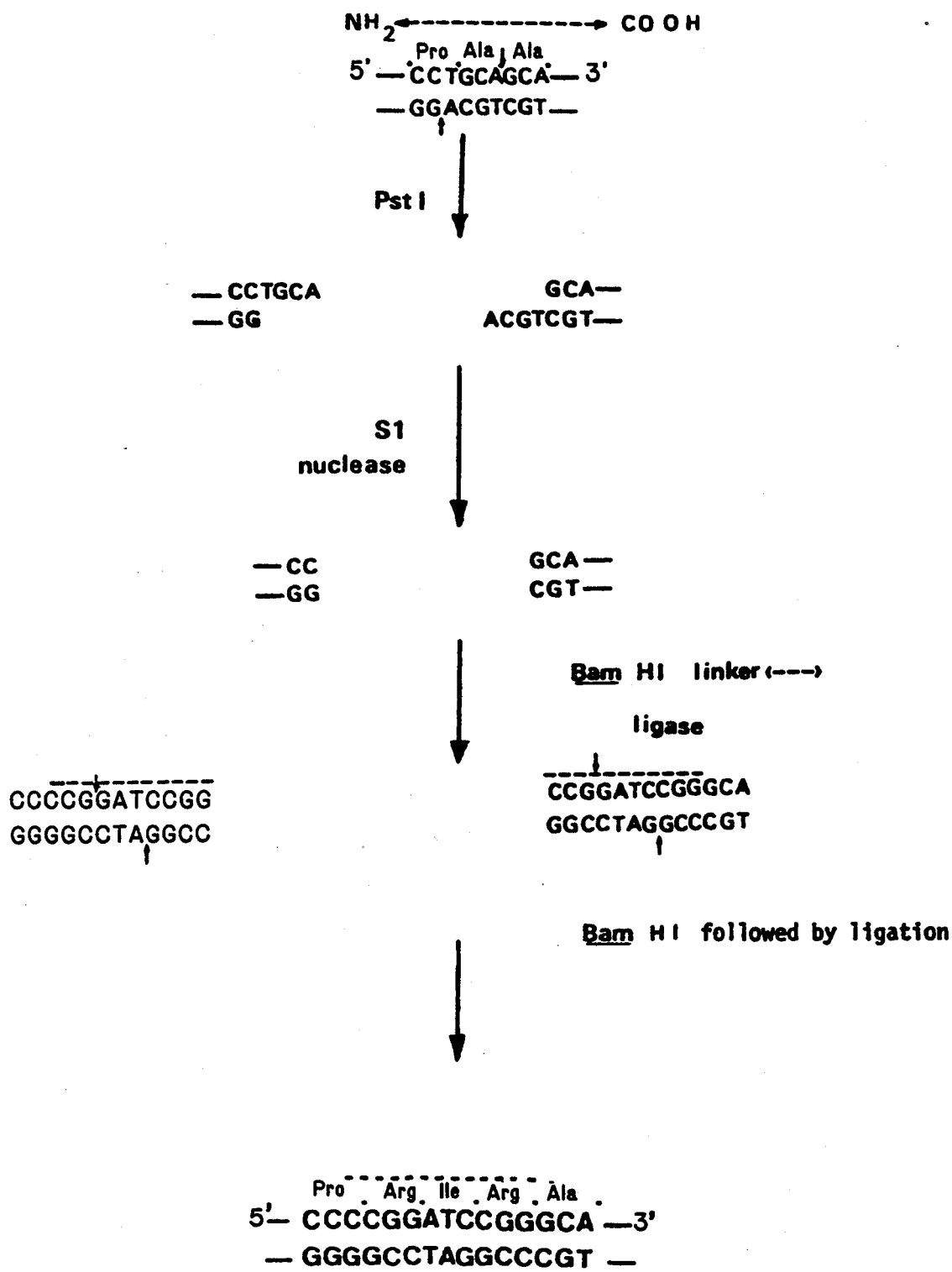
FIG. 7 displays the conversion of a PstI site in μ-lactamase to a BamHI site.

3. pPLa4 and pPLa8—Conversion Of The PstI Site In The β-Lactamase Gene Of pPLa2311 To A BamHI Site FIG. 3 and 7 display in schematic outline the conversion of the PstI site in the β-lactamase gene of pPLa2311 to a BamHI site. Plasmid pPLa2311 was linearized with PstI. Following phenol and chloroform extraction, the DNA was precipitated, redissolved to a concentration of 50 pmol/ml in 25 mM $NaCOOCH_3$ (pH 4.5), 1 mM $ZnCOOCH_3$, 125 mM NaCl and treated with S1 nuclease (Sigma) at 1.5 units per pmol of DNA for 90 min at 25° C. to remove the 3'-protruding ends (FIG. 7). The reaction was terminated by addition of EDTA to 5 mM. S1 nuclease was removed by incubating the mixture in the presence of 0.2% SDS for 10 min at 70° C. followed by phenol and chloroform extraction. The DNA was precipitated by addition of 4 vol 2 M $NH_4COOCH_3$ and 14 vol ethanol.

The recovered DNA was blunt-end ligated to a 10-fold molar excess of BamHI linker molecules (Collaborative Research Inc.) (C. Bahl et al. "A General Method For Inserting Specific DNA Sequences Into Cloning Vehicles", Gene, 1, pp. 81-92 (1977)) (FIG. 7). Following cleavage with BamHI and religation at low DNA concentration (FIG. 7), the mixture was cleaved with PstI to counterselect those molecules that had escaped S1 nuclease treatment and retained an intact PstI site. Two μg of treated DNA was then transformed into E. coli M5219 and transformants selected by kanamycin resistance. A total of 10 transformants was obtained, two of which lacked a PstI site and had acquired a BamHI site. The recombinant DNA molecules of these latter two transformants were designated pPLa8 and pPLa4 (FIG. 3, pPLa4 is not shown in FIG. 3). The fragments obtained after combined EcoRI-BamHI digestion of the recombinant DNA molecules of these transformants comigrated on a 1.4% agarose gel with the fragments obtained from pPLa2311 after ECoRI-PstI cleavage. Therefore, the PstI site in pPLa2311 has been replaced by a BamHI site.

Referring again to FIG. 7, the effect of the above-described sequence of steps on the β-lactamase gene is depicted. As illustrated in FIG. 7, the final result of the construction is the replacement of the Ala amino acid residue at position 182 in the β-lactamase protein by the sequence Arg-Ile-Arg. Since this substitution will leave the reading frame of the β-lactamase gene intact, it was expected that transformants of the reconstructed clones would display resistance to carbenicillin. Unexpectedly, host cells transformed with pPLa4 and pPLa8 were not resistant to carbenicillin.

4. pPLa83—Introduction Of A BamHI Site Next To The EcoRI Site Of pPLa8

Figure 4:
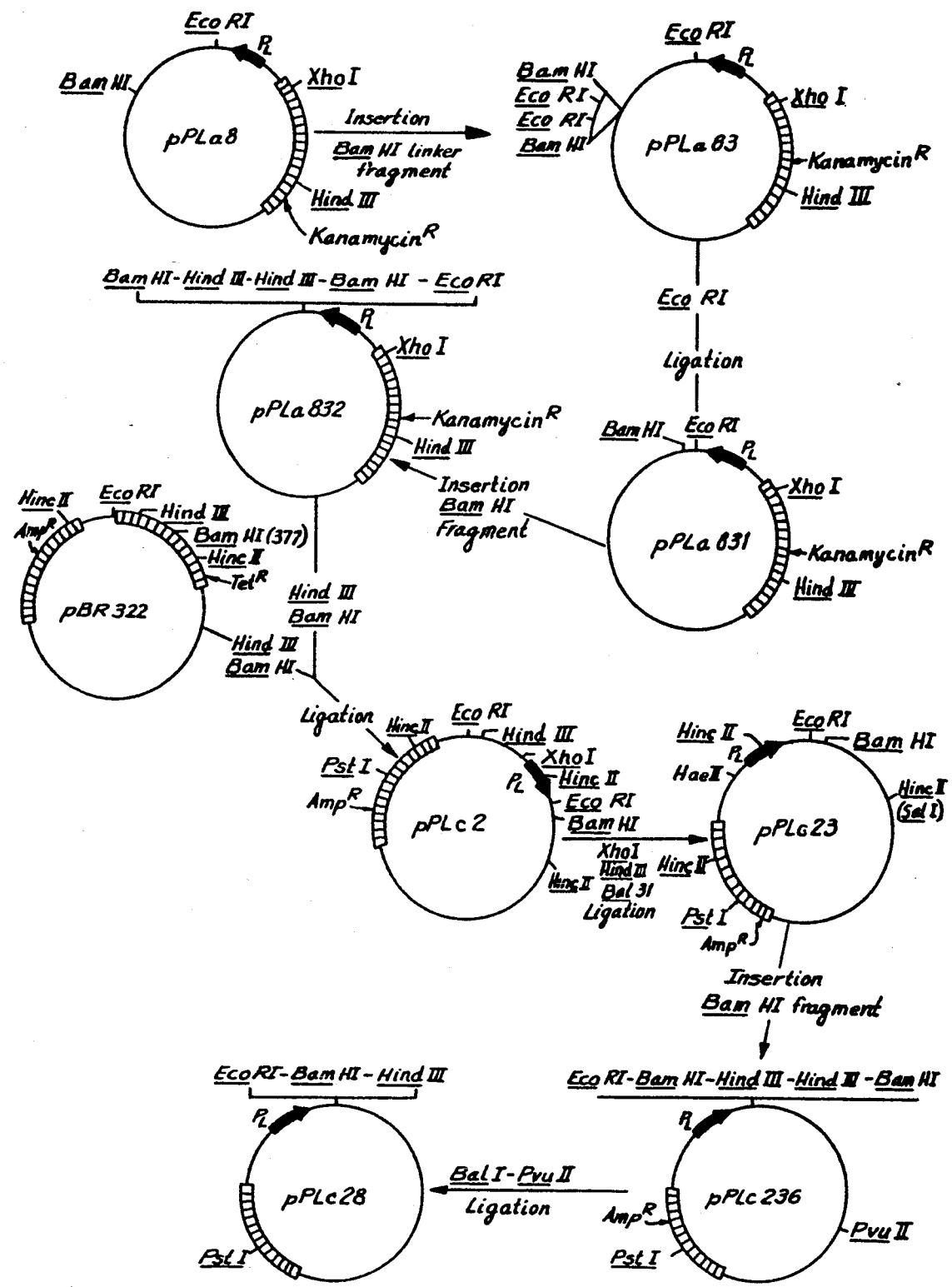
FIG. 4 is a schematic outline of the construction of vectors in accordance sith this invention—pPLa83, pPLa831, pPLa832, pPLc2, pPLc23, pPLc236 and pPLc28.

Plasmid pAD3 (a gift of H. Schaller) contains a 47 base pair sequence inserted into the BamHI site of pBR322. This sequence consists of the following units—BamHI site-EcoRI site-lactose operator-EcoRI site-BamHI site. In order to insert this sequence into the reconstructed BamHI site of pPLa8, pPLa8 and a 10-fold excess of pAD3 were digested with BamHI, religated and transformed into E. coli W6 ($λ_{rex}$) (FIG. 4). Transformants were selected on plates containing minimal medium, 50 μg/ml kanamycin, 0.1% glucose, 40 μg/ml×gal (5-bromo-4-chloro-3-indolyl-β-D-galactoside) (J. Miller, Experiments In Molecular Genetics (Cold Spring Harbor Laboratory), p. 48 (1972)), because the presence of ×gal dye allows detection of transformants which contain a lactose-operator fragment. In fact, in that medium lactose operator-containing transformants are blue and therefore easily distinguishable from other transformants.

The recombinant DNA molecules were isolated from one of the blue colonies, as before, and digested with EcoRI. The resulting two fragments substantially comigrated on agarose gel with the two fragments obtained from EcoRI-BamHI digestion of pPLa8, thereby confirming that the desired 47 base pair fragment from pAD3 had been correctly inserted at the reconstructed BamHI site in pPLaS. The plasmid was designated pPLa83 (FIG. 4).

5. pPLa831—Bringing A BamHI Site Closer To The $P_L$ Promoter In pPLa83

To bring a BamHI site closer to the $P_L$ promoter in pPLa83, the EcoRI-EcoRI fragment was deleted by digestion of pPLa83 with EcoRI and religation at dilute DNA concentration (FIG. 4). Transformation of the resulting recombinant DNA molecules into E. coli W6 ($λ_{rex}$) and growth on plates containing minimal medium supplemented as before with ×gal and kanamycin permitted selection of those clones no longer containing the lactose operator region. Restriction of the DNA from a selected transformant with BamHI-XhoI and a comparison of the migration of the resulting fragments with the two fragments obtained from EcoRI-XhoI digestion of pPLaS, confirmed that as expected the BamHI site in the modified plasmid was about 150 base pairs from the $P_L$ promoter. The modified plasmid was designated pPLa831.

It should of course be understood that manipulations similar to those described in any of 3, 4 and 5 above could be employed to provide other endonuclease recognition sites less than 300 base pairs from the chosen promoter and operators in the vectors of this invention. Examples of such manipulations include those described below.

6. pPLa832—Insertion Of A HindIII Site Next To the BamHI Site of pPLa831

Plasmid pAD16 (a gift of H. Schaller) contains a 36 base pair fragment inserted in the BamHI site of pBR322 consisting of: BamHI site-HindIII site-HindIII site-BamHI site. To insert this sequence at the BamHI site of pPLa831, pPLa831 and a 10-fold excess of PAD33 were cleaved with BamHI, religated and transformed into E. coli M5219 selecting for kanamycin resistance (FIG. 4). Since there is no easy screening method to determine proper insertion of the desired BamHI fragment into pPLa831, analysis of the transformants that grew in the presence of kanamycin depended on restriction cleavage of individual, randomly chosen clones. Among 32. clones analysed, one was found that produced two fragments after cleavage with HindIII (FIG. 4). The size of these fragments was indistinguishable on a 1.4% agarose gel from the fragments obtained after BamHI-HindIII cleavage or EcoRI-HindIII cleavage of pPLa831. This modified plasmid was designated pPLa832.

B. Vectors Containing The $P_L$ Promoter In The Clockwise Orientation With Respect To The Origin Of Replication 1. pPLc2—Cloning of The $P_L$ Carrying Fragment of pPLa832

An equimolar mixture of pBR322 and pPLa832 was cleaved with BamHI and subsequently with HindIII (FIG. 4). The mixture was religated and transformed into M5219 selecting for resistance to carbenicillin. Since correctly prepared recombinant DNA molecules of this construction no longer include the intact gene for tetracycycline, the transformants were also screened for loss of resistance to tetracycline. The recombinant DNA molecule was isolated as before from selected transformants and analyzed by restriction. The selected plasmid contained a single HindIII site. combined HindIII-BamHI digestion produced two fragments substantially comigrating on agarose gel with the two fragments produced by single EcoRI digestion. The presence of the $P_L$-carrying fragment was verified by HincII digestion. This enzyme cleaved the vector into three fragments, the sizes of which were consistent with the structure of the fragments shown in FIG. 4. This plasmid was designated pPLc2, the "c" serving to indicate the clockwise orientation of the $P_L$ promoter with respect to the origin of replication.

2. pPLc23—Removal of One EcoRI Site From pPLc2

Plasmid pPLc2 contains two EcoRI sites—one derived from the parent pBR322 vector and one close to the BamHI site introduced by inserting the HindIII-BamHI fragments from pPLa832 (FIG. 4). The EcoRI site derived from pBR322 was removed by cleaving pPLc2 with HindIII and XhoI followed by digestion with the Bal31 for 30 min at 25° C. in 0.6 M NaCl, 12.5 mM each $CaCl_2$ and $MgSO_4$, 1 mM EDTA, 20 mM Tris-HCl (pH 8.1). Exonuclease Bal31 degrades 3'- and 5'-termini in a stepwise fashion (H. Gray et al. "Extracellular Nucleases of Pseudomonas Bal31. I. Characterization Of Single Strand-Specific Deoxyriboendonuclease And Double-Strand Deoxyriboexonuclease Activities", *Nucleic Acids Res.*, 2, pp. 1459–92 (1975)).

The mixture was extracted with phenol and chloroform, diluted to a DNA concentration of 1 μg/ml and ligated. Following ligation, the DNA was again cleaved with XhoI and HindIII to eliminate parental plasmid molecules and transformed into M5219 selecting for resistance to carbenicillin. One transformant was found which lacked a HindIII and a XhoI site. This plasmid contained a single ECoRI site and possessed three HincII sites (FIG. 4). This latter property confirmed that the $P_L$ region was still present. This plasmid was designated pPLc23.

To assess the extent of exonucleolytic degradation by the Bal31 enzyme, pPLc23 DNA was cleaved simultaneously with BamHI and PstI and the fragments sized on a 1.4% agarose gel. Compared to the PstI-BamHI fragment form the parent pPLc2 the PstI-BamHI fragment from pPLc23 displayed an over 800 base pairs deletion. Combined digestion with EcoRI-PstI-HaeII as compared to EcoRI-PstI cleavage confirmed that the HaeII site at the junction between the $P_L$-carrying fragment and the kanamycin fragment had been maintained.

3. pPLc236—Introduction of a HindIII Site In pPLc23

Plasmid pPLc23 contains unique ECoRI and BamHI sites located about 150 nucleotides downstream from the $P_L$ promoter (FIG. 4). A HindIII insertion site was introduced into pPLc23 by ligating the BamHI-HindIII-HindIII-BamHI fragment obtained from pPLa832 into the BamHI site of pPLc23. Transformants were obtained in M5219 and screened by restriction analysis for the presence of a HindIII site. The structure of a representative clone was confirmed by agarose gel electrophoresis of the fragments obtained after PStI-EcoRI, PstI-BamHI or PstI-HindIII digestion. The fragments obtained after each of these combined digestions substantially comigrated on a 1.4% agarose gel showing that the EcoRI, BamHI and HindIII sites are localized in the immediate vicinity of each other. This plasmid was designated pPLc236 (FIG. 4).

The larger part of plasmid pPLc236 is derived from pBR322 from the BamHI site at position 377 (J. Sutcliffe, supra) up to at least the start of the β-lactamase gene around position 4160 (J. Sutcliffe, supra). The remaining part is composed of 1) sequences derived from part of the kanamycin gene situated between the XhoI site and one HaeII end of this fragment; 2) a HaeII-BamHI fragment containing the $P_L$ promoter, comprising about 300 nucleotides and derived from pPLa832; 3) a sequence coding for BamHI-HindIII-HindIII-BamHI sites.

4. pPLc28—Deletion From pPLc236

Overlapping the two adjacent HindIII sites in pPLc236 is a BalI site (not shown in FIG. 4). The plasmid also contains a unique pvuII site at base pair 2067 of the pBR322 portion (J. Sutcliffe, supra) (FIG. 4). The enzymes BalI and PvuII both produce flush ends. pPLc236 DNA was cleaved with BalI and PvuII and religated at low DNA concentration. Transformants were obtained in M5219 selecting for resistance to carbenicillin. DNA of a representative clone was analyzed by restriction. BamHI cleavage produced a single fragment comigrating on 1.4% agarose gel with the larger part of pPLc236 after BamHI-PvuII cleavage. Combined digestion with either PstI-EcoRI, PstI-BamHI or PstI-HindIII in each case produced two fragments, the smaller of which substantially comigrated on a 1.4% agarose gel with a PstI-EcoRI fragment obtained from pPLc236. This plasmid was designated pPLc28 (FIG. 4).

pPLc28, like the other plasmids described in accordance with this invention, may of course be further manipulated to insert other restriction sites. For example, a fragment containing the following: Xba restriction site—Sal restriction site—Xba restriction site Pst restriction site—Xba restriction site has been inserted in pPLc28 at the HindIII restriction site. This plasmid was designated pPLc2819. Another like manipulation afforded a plasmid containing the fragment Pst restriction site—Sal restriction—Xba restriction site—Sal restriction site—Xba restriction site inserted at the BamHI site of pPLc28. This plasmid was designated pPLc2833.

5. pPLc24—Insertion Of The Ribosome-Binding Site And The Amino-Terminal Part Of Bacteriophage MS2 Relicase Protein Into pPLc28

Figure 5:
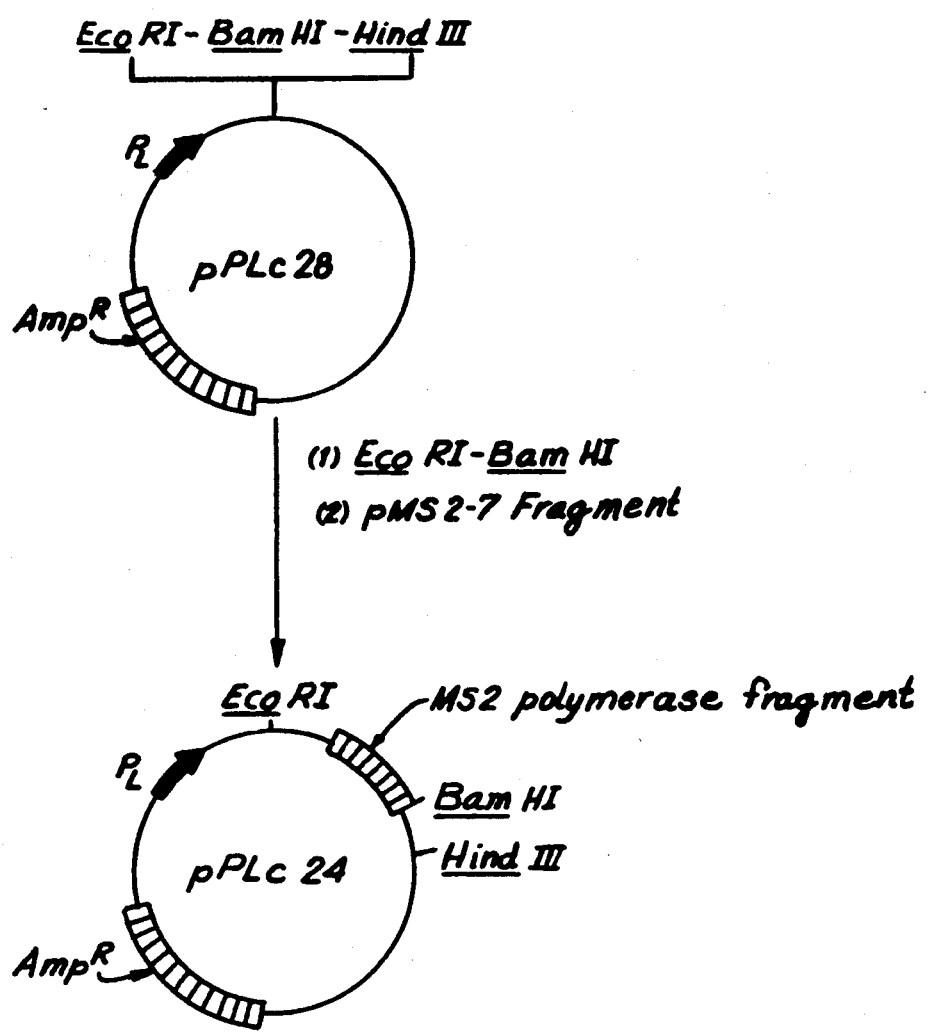
FIG. 5 is a schematic outline of the construction of vectors in accordance with this invention—pPLc24.

A 431 base pair EcoRI-BamHI fragment, coding for the ribosome binding site and the first 98 amino acid residues of the bacteriophage MS2 replicase gene was obtained from plasmid pMS2-7 (R. Devos et al., "Construction And Characterization Of A Plasmid Containing A Nearly Full-Size DNA Copy Of Bacteriophage MS2 RNA", *J. Mol. Biol.*, 128, pp. 595–619 (1979)). This fragment was inserted into plasmid pPLc28 replacing the original EcoRI-BamHI fragment therein (FIG. 5). The structure of the resulting plasmid, designated pPLc24, was verified by restriction analysis with EcoRI-BamHI and size comparison of the resulting fragments with those obtained after EcoRI-BamHI digestion of pMS2-7 and pPLc28. In pPLc24 translation of the MS2 replicase protein fragment runs colinearly with the transcription from the $P_L$ promoter and hence is under $P_L$ control.

BIOLOGICAL PROPERTIES OF HOST CELLS TRANSFORMED BY THE VECTORS OF THIS INVENTION

1. Stability At 28° C.

Strains K12ΔHI or M5219 transformed with any of the above described vectors were grown at 28° C. for 20 generations in LB medium without selection for the antibiotic resistance marker. Suitable dilutions of the cultures were then plated at 28° C. either in the presence or the absence of the desired antibiotic. In all cases the number of colonies obtained was the same regardless of the selection for the antibiotic resistance, demonstrating that the vectors were fully stable in these hosts at 28° C. (see Table I, infra).

All vectors could also be transformed into a host strain lysogenic for bacteriophage λ. Such strains where the resident phage synthesizes a wild-type cI product were viable at elevated temperature (37° C.). In contrast, non-lysogenic hosts could not be transformed with these vectors. Instead, the rare transformants obtained from these experiments invariably contained vectors with deletions removing all or most of the $P_L$ region.

2. Behavior Of Cells Containing $P_L$ Vectors After Prolonged Induction At 42° C.

The efficiency of plating at 42° C. of strains K12ΔHI and M5219 transformed with the vectors of this invention was determined either in the presence or absence of antibiotic selection.

Vectors having the $P_L$ inserted in the clockwise orientation with respect to the origin of replication (pPLc-type) behaved similarly. The results obtained with pPLc236 are listed in Table I, infra. Strain K12ΔHI transformed with pPLc236 plated equally well at 42° C. as at 28° C. regardless of whether antibiotic selection was applied or not. Strain M5219 transformed with pPLc236 plated on non-selective plates with an efficiency of 1. However, when antibiotic selection was applied, the efficiency of plating dropped at least 1000-fold. Colonies obtained at 42° C. on non-selective plates no longer carried resistance to the antibiotic marker.

Vectors having the $P_L$ inserted in the anti-clockwise orientation with respect to the origin of replication (pPLa-type) displayed a more complex pattern of colony formation at 42° C. Transformants of strain M5219 did not form colonies at 42° C. even in the absence of antibiotic selection (the efficiency of plating was less than $10^{-3}$; Table I). The behavior of transformants of strain K12ΔHI at 42° C. depended on the nature of the vector present. For example, whereas transformants containing pPLa832 invariably displayed at least a 1000-fold reduction of plating efficiency, both with and without antibiotic selection, transformants containing pPLa23 or pPLa2311 displayed plating efficiencies ranging from 1 to $10^{-3}$, frequently with wide heterogeneity in colony size.

Therefore, expression of pPLa-type vectors at 42° C. causes interference with host metabolism, making the cells unable to survive at this high temperature, even in the absence of selection for the plasmid. This effect is most pronounced using M5219 hosts. Conversely, pPLc-type vectors do not interfere directly with host cell metabolism because 100% survivial of induced cells in the absence of selective pressure is observed. Continued transcription from the $P_L$ promoter concomitant with expression of the N gens in M5219 may, however, result in inhibition of vector replication in M5219 strains. This is illustrated by the inability of such cells to grow at 42° C. on selective plates.

TABLE I

| | | Plating efficiency* | | | |
|---|---|---|---|---|---|
| | | 28° C. | | 42° C. | |
| Strain | Vector | Without selection | With selection | Without selection | With selection |
| K12ΔHI | none | 1 | — | 1 | — |
| | pPLa23 | 1 | 1 | 1 to $\leq 10^{-3}$ | 1 to $\leq 10^{-3}$ |
| | pPLa2311 | 1 | 1 | 1 to $\leq 10^{-3}$ | 1 to $\leq 10^{-3}$ |
| | pPLa832 | 1 | 1 | $\leq 10^{-3}$ | $\leq 10^{-3}$ |
| | pPLc236 | 1 | 1 | 1 | 1 |
| M5219 | none | 1 | — | 1 | — |
| | pPLa23 | 1 | 1 | $\leq 10^{-3}$ | $\leq 10^{-3}$ |
| | pPLa2311 | 1 | 1 | $\leq 10^{-3}$ | $\leq 10^{-3}$ |
| | pPLa832 | 1 | 1 | $\leq 10^{-3}$ | $\leq 10^{-3}$ |
| | pPLc236 | 1 | 1 | 1 | $\leq 10^{-3}$ |

*Bacterial cultures were grown to saturation in LB medium at 28° C. in the presence of antibiotic. Suitable dilutions were plated either in the presence or absence of antibiotic and incubated at 28° C. or 42° C. The number of colonies obtained was determined.

EXPRESSION OF GENES IN THE VECTORS OF THIS INVENTION

1. General Procedure

The vectors of this invention may be usefully employed to produce a variety of polypeptides and proteins by inserting DNA sequences comprising genes coding for the desired polypeptides or proteins into the vectorsat one of the endonuclease recognition sites adjacent to the promoter and operator, transforming appropriate hosts with vectors containing those inserted DNA sequences, culturing the hosts and collecting the polypeptides or protein products. Examples of such polypeptides and proteins include leukocyte interferon, insulin, antigens of hepatitis, antigens of foot and mouth disease, fibro-blast interferon, human growth hormone, animal growht hormone immune interferon and a variety of other prokaryotic, eukaryotic and viral enzymes, hormones, polypeptides, antigens and proteins.

To illustrate these processes, the synthesis of specific gene products in the vectors of this invention was monitored by pulse-labelling of induced cells and analysis of the labelled proteins by polyacrylamide gel electrophoresis.

Cells transformed with the vectors of this invention were grown in LB medium without antibiotic at 28° C. to a density of $2 \times 10^8$/ml. The cells were collected by centrifugation and resuspended in the original volume of a medium consisting of 19 mM NH$_4$Cl, 86 mM NaCl, 42 mMNa$_2$HPO$_4$, 1 mMMgSO$_4$, 0.2% glucose, 0.05% casamino acids (Difco), 0.01% yeast extract and 50 µg/ml/L-tryptophan for labelling of the cells with $^{14}$C-amino acid mixture or the above medium except for a substitution of 5% methionine assay medium (Difco) for the casamino acids and yeast extract for labelling of the cells with $^{35}$-methionine. Incubation at 28° C. was continued for 60 min. One-half of the culture was then shifted to 42° C. At various times after induction, as indicated by the number of minutes set forth above the lanes in FIGS. 8-11 aliquots from the 28° C. and 42° C. cultures were labelled with $^{14}$C-amino acid mixture or with $^{35}$S-methionine (Amersham).

Incorporation of label was terminated by phenol extraction. The synthesized proteins were precipitated from the phenol layer by addition of 5 vol ethanol and redissolved in 1% SDS, 1% β-mercaptoethanol, 10% glycerol, 62.5 mM Tris-HCl (pH 6.8). Samples were boiled for 5 min, centrifuged at 12000×g and electrophoresed in SDS-containing polyacrylamide gels (10% to 15% acrylamide) according to the procedure of U.-Laemmli, "Cleavage Of Structural Proteins During the Assembly Of The Head 0f Bacteriophage T4", *Nature*, 227, pp. 680-82 (1970). Following electrophoresis, the gels were prepared for fluorography according to the method of W. Bonner & R. Laskey, "A Film Detection Method For Tritium-Labelled Proteins And Nucleic Acids In Polyacrylamide Gels", *Eur. J. Biochem.*, 46, pp. 83-88 (1974) except that EN$^3$HANCE (NEN) was employed instead of PPO-DMSO.

2. Prokaryotic Genes
   (a) The β-Lactamase Gene pPLa23 (FIG. 3) includes the β-lactamase gene in the sense orientation downstream from the P$_L$ promoter. Therefore, production of the protein coded for by the β-lactamase gene can be monitored as an indication of the efficiency of the vector in expressing prokaryotic genes.

Transformants of K12ΔHI and M5219 with pPLa23—*E. coli* K12ΔHI (pPLa23) and *E. coli* M5219 (pPLa23)—were prepared as described previously and their protein synthesis monitored. The results are displayed in FIG. 8. There, it can be seen that a dramatic increase in the rate of synthesis of two proteins with apparent molecular weights of 27.5K and 30K, respectively, occurred shortly after induction of the transformants at 42° C. The sizes of these expressed proteins are consistent with the expected length of mature β-lactamase and its precursor (J. Sutcliffe, supra). Moreover, induced synthesis of these proteins was paralleled by an increasing enzymatic activity of β-lactamase as determined by the method of O'Callaghan et al., "Novel Method For Detection Of β-Lactamases By Using A Chromogenic Cephalosporin Substrate", *Antimicrobial Agents and Chemotherapy*, 1, pp. 283-88 (1972) and both proteins were specifically precipitated by anti-β-lactamase serum. As a control, the protein synthesis in hosts not transformed with vector pPLa23 was monitored. Synthesis of neither of the two above described proteins was observed from these non transformed hosts.

As shown in FIG. 8, the overall pattern of protein synthesis in these transformants is very similar at 28° C. and 42° C. However, the rate of synthesis of some proteins appears to be altered significantly by shifting the cells to 42° C. Similar behavior has been observed in cells not transformed with pPLa23. In addition, as shown in FIG. 8, the relative amount of the larger of the two β-lactamase related proteins—the unprocessed precursor for β-lactamase—becomes greater with time after induction. This skewing towards a build-up of precursor protein may indicate a saturation of the β-lactamase processing machinery of the cell.

To determine the percentage synthesis of β-lactamase as compared to total de novo protein synthesis of the transformant, the protein bands for the β-lactamase (27.5K) and its precursor (30K) were excised from the dried gel and their radioactivity compared to the total radioactivity applied to the gel. These results are displayed in Table II.

TABLE II

Percentage Synthesis Of β-lactamase As Compared To Total De Novo Protein Synthesis

| Minutes after induction at 42° C. | Strain K12ΔHI | M5219 |
|---|---|---|
| 0-10 | 8% | 9% |
| 10-20 | 9% | 16% |
| 20-30 | 10% | 25% |
| 30-40 | 16% | 24% |
| 40-50 | 23% | 30% |
| 50-60 | 27% | — |
| 60-70 | 30% | — |
| 70-80 | 33% | — |
| control at 28° C. | 5% | 4% |

As shown in Table II, synthesis of β-lactamase and its precursor reaches a maximum level of about 30% of total de novo protein synthesis in both host cell strains. However, the kinetics of reaching this level are different for the two strains—strain K12ΔHl lags about 20 min behind strain M5219 in attaining the 30% level. While not wishing to be bound by theory, it may be that the N gene product, co-produced upon induction of strain M5219 but absent in strain K12ΔHl, may overcome certain transcription slow-down signals in the DNA sequences downstream from the P$_L$ promoter and thereby speed β-lactamase synthesis in strain M5219.

To determine the rate of total protein synthesis in these transformants, total radioactivity incorporated during a specific time interval was determined and compared to that incorporated during the 0-10 min interval (i.e., that initial interval being arbitrarily chosen as 100% for a reference). The results are displayed in Table III.

TABLE III

Rate Of Total Protein Synthesis

| Minutes after induction at 42° C. | Strain K12ΔHI | M5219 |
|---|---|---|
| 1-10 | 100% | 100% |
| 10-20 | 104% | 92% |
| 20-30 | 134% | 56% |
| 30-40 | 113% | 31% |
| 40-50 | 120% | 10% |
| 50-60 | 113% | 7% |
| 60-70 | 96% | 3% |
| 70-80 | 96% | 3% |
| 150-160 | 20% | — |

As shown in Table III, total protein synthesis in *E. coli* M5219 (pPLa23) is rapidly shut down after induction. This is consistent with the previously observed failure of M5219 transformants to survive 42° C. No similar inhibition of protein synthesis is observed in *E. coli* M5219 (pBR322). A substantial reduction in total protein synthesis is also observed in *E. coli* K12ΔHI (pPLa23) after prolonged incubation at 42° C. However, these cells are able to survive 42° C. temperatures.

(b) The Tryptophan Synthetase A Gene (i) pPLa23

An EcoRI fragment (5300 b.p.) containing the trp A cistron of Salmonella typhimurium was obtained from pES9 (E. Selker et al., "Mitomycin C Induced Expression Of trp A Of Salmonella tryphimurium Inserted Into The. Plasmid ColEl", J. Bacteriology, 129, pp. 388–94 (1977)) and inserted into pPLa23 at its EcoRI site. Two representative plasmids having this fragment inserted in either of the two possible orientations with respect to the direction of the $P_L$ promoter were designated pPLa23trpA$_1$ and pPLa23trpA$_2$.

Induction profiles of strain K12ΔHI containing either pPLa23trpA$_1$ or pPLa23trpA$_2$ are shown in FIG. 9. A major protein of about 25000 daltons was induced by pPLa23trpA$_1$ but was absent from induced cells containing pPLa23trpA$_2$. The observed molecular weight of this protein is consistent with the theoretical value (28500) predicted from the nucleotide sequence of the S. typhimurium trp A gene (B. Nichols & C. Yanofsky, "Nucleotide Sequences Of trp A Of Salmonella tryphimuriumAnd Escherichia coli: An Evolutionary Comparison", Proc Natl. Acad. Sci. U.S.A., 76, pp. 5244–48 (1979). Moreover, enzyme activity consistent with the presence of a trp A gene product, as determined according to the procedures of O. Smith & C. Yanofsky "Enzymes Involved In The Biosynthesis Of Tryptophan", Methods in Enzymology, 5, pp. 794–806, (1962) increased in parallel with the accumulation of this induced protein.

After prolonged induction of both pPLa23trpA$_1$ and pPLa23trpA$_2$ a protein with an approximate molecular weight of 18K is synthesized (FIG. 9). The percentage synthesis of this protein as compared to total de novo protein synthesis of the transformant is independent of the orientation of the EcoRI trp A fragment with respect to the direction of transcription from the $P_L$ promoter. Therefore, presumably the synthesis of this protein is controlled by a, perhaps slightly temperature-dependent, bacterial promoter present on the 5300 base pair EcoRI trp A fragment whose coding capacity is indeed much larger than needed for trp A. (E. Selker, supra).

The percentage synthesis of trp A as compared to the total de novo protein synthesis in the transformant was determined substantially as described previously for β-lactamase. The results are displayed in Table IV. Again, trp A synthesis reached a maximum level of about 30% of total de nove synthesis.

TABLE IV

| | Percentage Synthesis Of trp A As Compared To Total De Novo Protein Synthesis | |
|---|---|---|
| Minutes after induction at 42° C. | K12ΔHI/ pPLa23A$_1$ | K12ΔHI/ pPLa23A$_2$ |
| 0–10 | 3% | 2% |
| 30–50 | 4% | 2% |
| 60–80 | 14% | 1% |
| 90–110 | 21% | 2% |
| 120–140 | 24% | 2% |
| 150–170 | 33% | 2% |
| control at 28° C. | 2% | 3% |

(ii) pPLa2311

A recombinant DNA molecule identical to pPLa23trpA$_1$, but based on pPLa2311, was also prepared substantially as described previously. K12ΔHI transformants with pPLa2311trpA$_1$, behaved similarly to those of pPLa23trpA$_1$ (except that in this experiment the maximum level of total de novo synthesis was only 20% after 150 min). Again, prolonged induction led to a net decrease in total protein synthesis.

(iii) pPLc23

The EcoRI fragment of pES9 has one end situated within the trp B gene and contains a single SalI site about 2500 base pairs from the EcoRI site (E. Selker et al., supra). Since the trp A gene does not contain a SalI site (B. Nichols & C. Yanofsky, supra), the trp A gene must be located completely in that portion of the EcoRI fragment of pES9 extending from the first EcoRI site to the SalI site. Therefore, the previously-prepared EcoRI fragment of pES9 was digested with SalI and the resulting fragment inserted into pPLc23 as a replacement to the EcoRI-SalI fragment therein (FIG. 4). Based on the observed direction of translation of the trp A gene in pPLa23trpA$_1$, and pPLa23trpA$_2$, the pPLc23-based recombinant DNA molecule having the trp A gene colinear with transcription from the $P_L$ promoter was designated pPLc23trpA$_1$.

Figure 10:
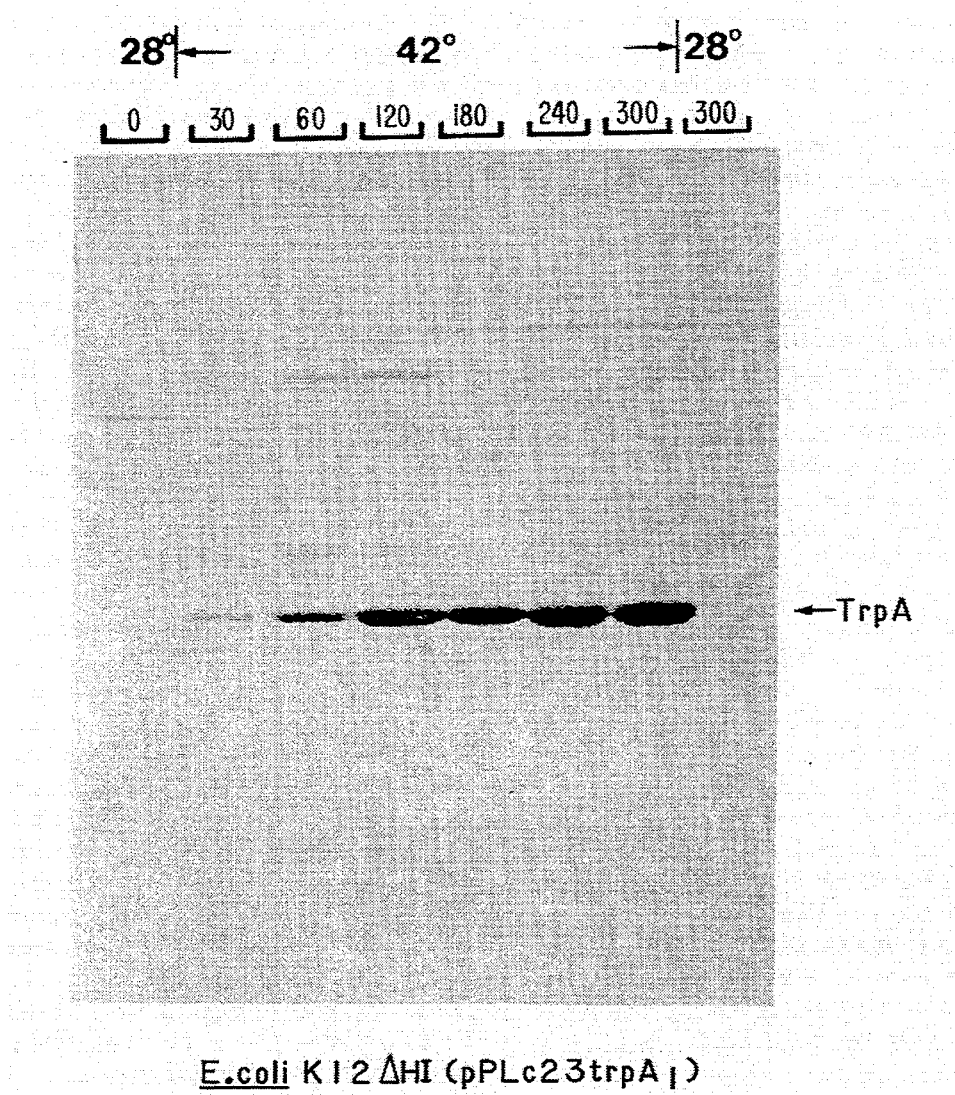
FIG. 10 is an autoradiograph monitoring protein synthesis at 28° C. and 42° C. in *E. coli* K12ΔHI (pPLc23trpA₁).

Upon induction (42° C.) of E. coli K12ΔHI (pPLc23trpA$_1$), trp A was synthesized to a maximum level of about 40% of total de novo protein synthesis after 3 h of induction. Moreover, this high level of de novo synthesis was maintained for 2 h (FIG. 10). These results are displayed in Table V, infra. Therefore, in contrast to the behavior of the pPLa-type vectors, the protein synthesis of the pPLc-type transformants does not decrease until up to 5 h after induction.

TABLE V

| Minutes after induction at 42° C. | Percentage synthesis of trp A* | Rate of total protein synthesis |
|---|---|---|
| 30–50 | 11% | 100% (reference) |
| 60–80 | 17% | 198% |
| 120–140 | 31% | 228% |
| 180–200 | 41% | 162% |
| 240–260 | 36% | 205% |
| 300–320 | 39% | 213% |
| control at 28° C. (300–320) | 3% | — |

*As compared to total de novo protein synthesis

The actual amount of induced protein accumulating in the above transformants was also measured by continuous labelling of the induced cells. E. coli K12ΔHI (pPLc23trpA$_1$) was grown at 28° C. in LB medium to a density of $1 \times 10^7$ cells/ml. The cells were then labelled with 10 μCi $^{14}$C-amino acid mixture. At a culture density of $4 \times 10^7$ cells/ml, the cells were shifted to 42° C. and incubation continued. When the culture reached saturation (6 h after induction), the proteins were extracted from the cells and separated on SDS-polyacrylamide gels. The percentage of radioactivity incorporated in the trp A band was determined. Under the conditions used it can be assumed that the cells have been uniformly labelled so that the radioactivity incorporated in a protein reflects the actual amount of that protein present in the cell. The trp A protein was found to account for 10% of total cell proteins.

This 10% concentration of trp A in the total cell proteins of E. coli K12ΔHI (pPLc23trpA$_1$) also serves to demonstrate the important differences between the λ $P_L$ containing vectors of H. Bernard et al., supra, and those of the present invention. In contrast to the 10% actual trp A concentration afforded by vectors of this invention, H. Bernard et al. report only a 6.6% concentration of trp A—estimated on the basis of trp A enzymatic activity and an assumed specific activity for the protein. It is also to be noted that the 6.6% trp A concentration reported by H. Bernard et al. was observed with vectors which also included an active N-gene and therefore presumably transcription was had in the presence of the anti-terminating N gene product. Only a 2% trp A concentration was reported by H. Bernard et al. with a vector that did not include an active N-gene. In contrast, the 10% trp A concentration observed with improved vectors of this invention was had in the absence of N-gene products. Therefore, the present vectors and methods constitute a marked improvement over those vectors and methods described in the art.

(c) The Bacteriophage MS2 Replicase Protein Gene

Plasmid pMS2-7 contains a nearly full-size copy of the genome of the RNA bacteriophage MS2 (R. Devos et al., supra). The phage replicase gene (R) is contained within an EcoRI-PstI fragment. This fragment was inserted into pPLa2311 by simple replacement of the EcoRI-PstI fragment of this vector. Transformants $E.$ $coli$ K12$\Delta$HI (pPLa2311R$_1$) were screened for sensitivity to carbenicillin since the gene for ampicillin resistance is no longer intact in pPLa2311R$_1$. The identity of the inserted fragment was established by coelectrophoresis on agarose gels with the known fragments from pMS2-7 DNA. In pPLa2311R$_1$, transcription of the MS2 replicase protein runs colinearly with transcription from the P$_L$ promoter.

Figure 11:
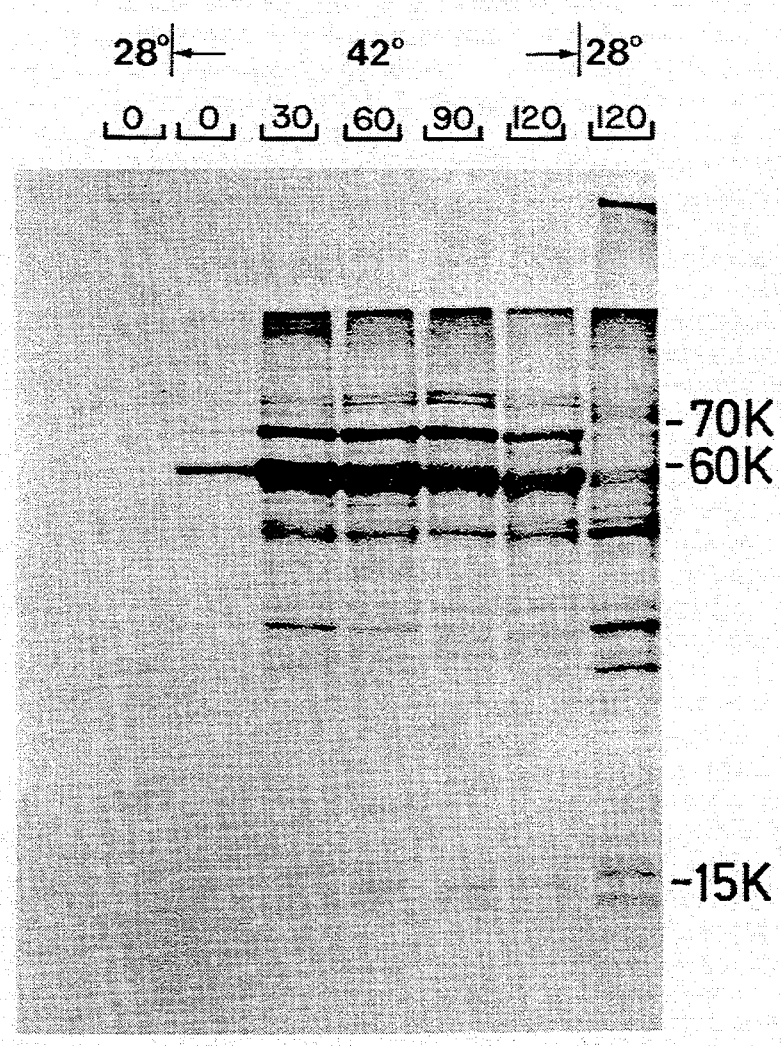
FIG. 11 is an autoradiograph monitoring protein synthesis at 28° C. and 42° C. in *E. coli* K12ΔHI (pPLa2311R₁).

Induced cells of $E.$ $coli$ K12$\Delta$HI (pPLa2311R$_1$) synthesize a protein with an apparent molecular weight of 59K (FIG. 11). The size of this protein is consistent with the 60692 daltons molecular weight, calculated for the MS2 replicase from sequence data of the viral RNA (W. Fiers et al., "Complete Nucleotide Sequence Of Bacteriophage MS2 RNA: Primary And Secondary Structure Of The Replicase Gene", Nature, 260, pp. 500–507 (1976)).

The presence of functional MS2 replicase protein in the protein products of cells transformed with pPLa2311R$_1$ was also verified by complementation analysis with MS2 amber mutants. This analysis confirmed that cells transformed with pPLa2311R$_1$ produced a product that specifically complemented the product of an MS2 mutant carrying a lesion in the replicase gene and that cells not transformed with pPLa2311R$_1$ did not complement the product of such mutant.

With respect to MS2 replicase protein synthesis, both $E.$ $coli$ K12$\Delta$HI (pPLa2311R$_1$) and $E.$ $coli$ M5219 (pPLa2311R$_1$) behaved similarly—after 30 min induction the percentage synthesis of MS2 replicase was 29% of total de novo protein synthesis, with the level of protein synthesis dropping rapidly upon further induction (FIG. 11). Since such decrease in the level of synthesis was not observed in the synthesis of $\beta$-lactamase or trp A, the reduction may be caused by a peculiar property of the MS2 replicase. For example, the observed tendency of phage replicase to bind to its own mRNA at a site near the middle of the cistron (Meyer et al., "The Binding Sites Of Q$\beta$ RNA", Experienta, 31, pp. 143 et seq. (1975)) may interfere with further translation of the complexed mRNA.

3. Eukaryotic Genes (a) The Small-t Antigen Of Simian Virus 40 Gene

Figure 12:
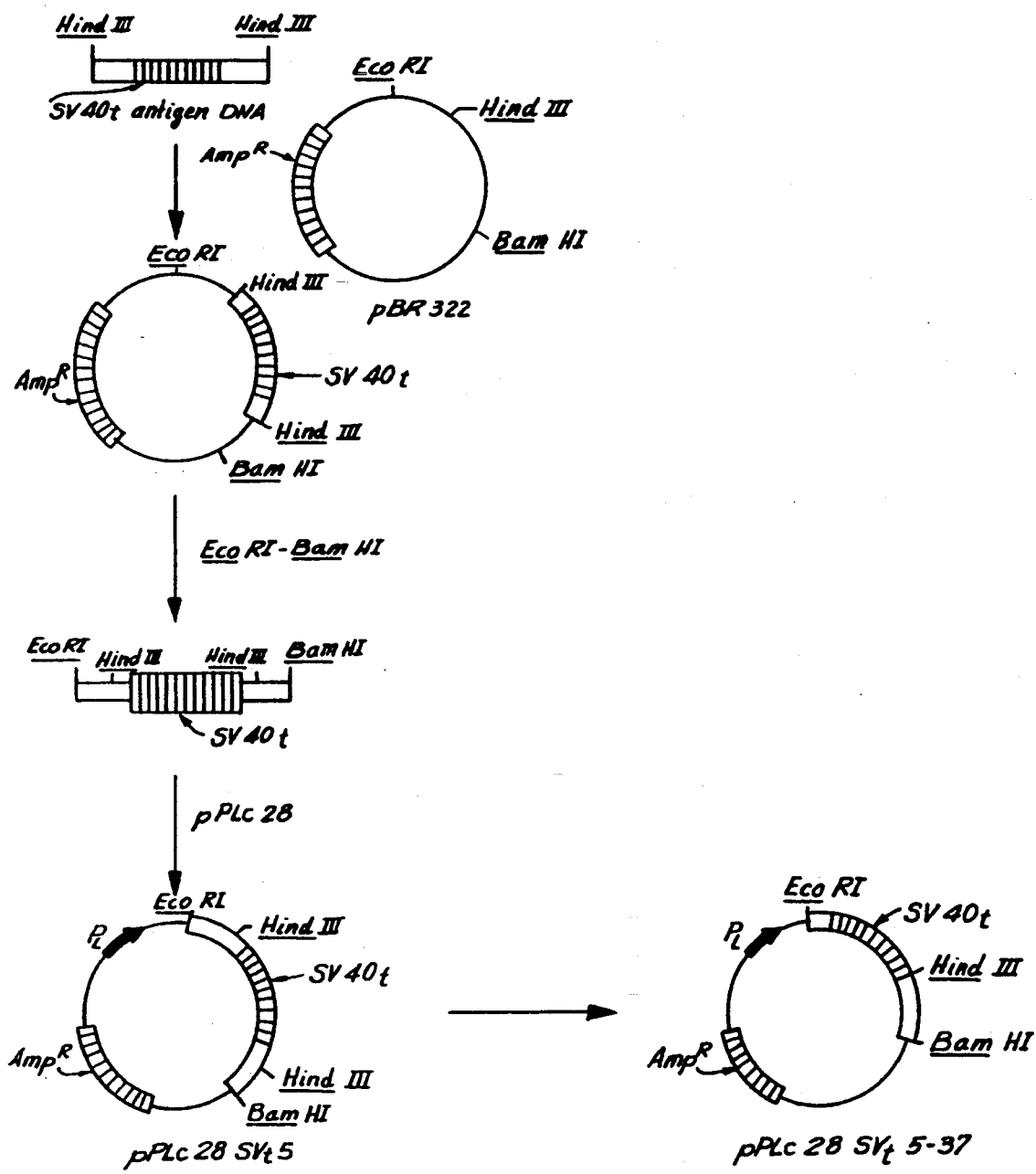
FIG. 12 is a schematic outline of the construction of pPLc28SV$_t$5 and pPLc28SV$_t$5-37.

A HindIII DNA fragment containing the complete coding sequence for the SV40 small-t antigen (G. Volckaert et al., "Nucleotide Sequence Of The Simian Virus 40 Small-t Gene", Proc. Natl. Acad. Sci. U.S.A., 75, pp. 2160–64 (1978)) was inserted into the HindIII site of pBR322 (FIG. 12). The orientation of the insert was determined by restriction analysis based on the presence of an asymmetrically-located TaqI site. From this hybrid DNA molecule an EcoRI-BamHI fragment encompassing the above-mentioned HindIII fragment and portions of pBR322 was excised and inserted into pPLc28, as a replacement for its EcoRI-BamHI fragment, such that the sense of translation of the small-t antigen runs colinearly with transcription from the P$_L$ promoter (FIG. 12). The resulting recombinant DNA molecule was designated pPLc28SV$_t$5.

Figure 13:
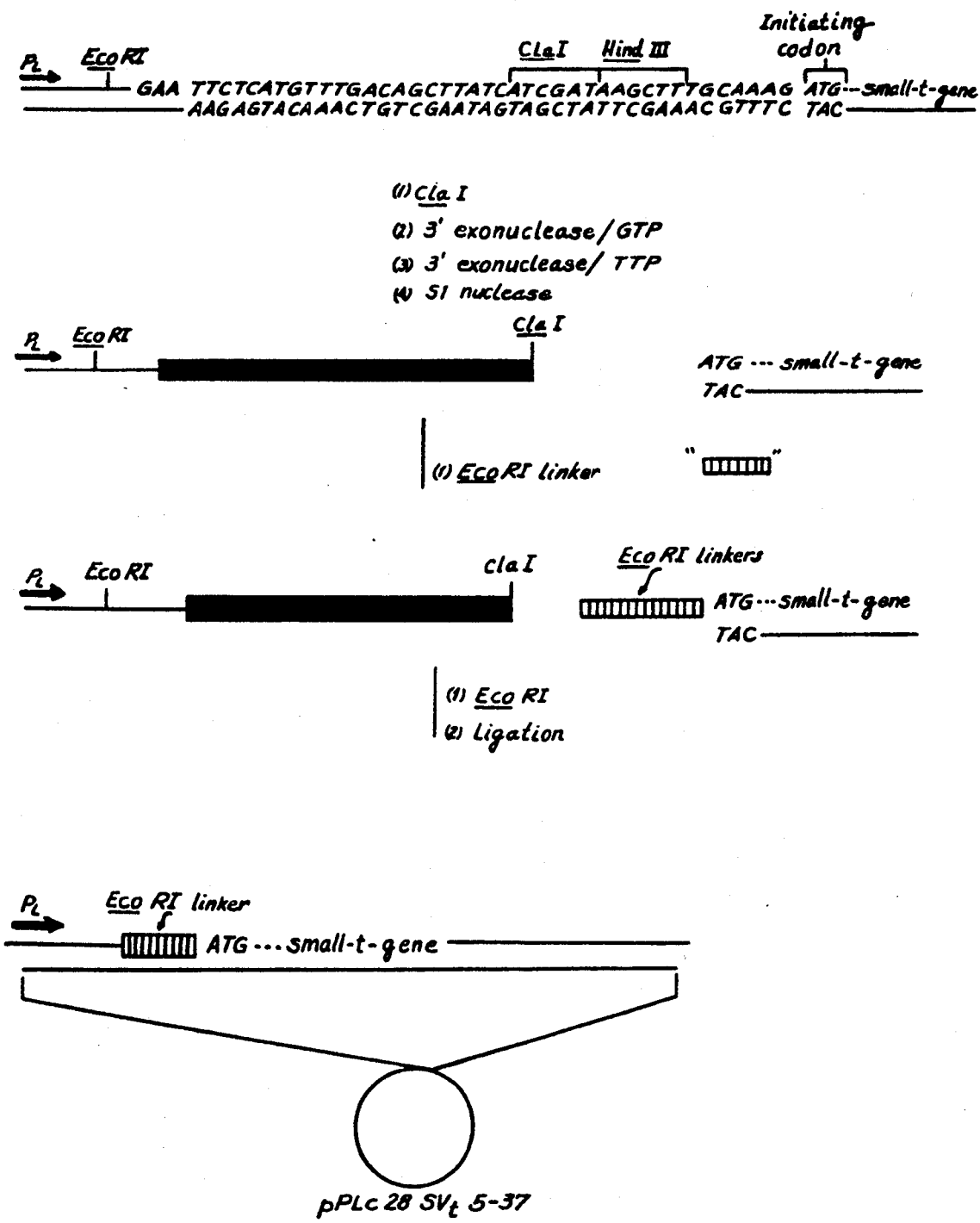
FIG. 13 displays the construction of pPLc28SV$_t$5-37 from pPLc28SV$_t$5 on the nucleotide level.

To shorten the distance between the P$_L$ promoter and the initiating codon (ATG) of the gene coding for small-t antigen, pPLc28SV$_t$5 was modified to eliminate the EcoRI-HindIII fragment between the gene and the P$_L$ promoter. These manipulations are depicted in FIGS. 12 and 13. They consisted of cleaving pPLc28SV$_t$5 with ClaI, chewing back the 3' end of the DNA in two separate steps using the 3' exonuclease activity of T4 DNA polymerase in the presence of GTP and TTP, respectively, further treatment with S1 nuclease, adding EcoRI linkers to the blunt end, cleaving the fragment with EcoRI and religating the complementary ends.

Figure 14:
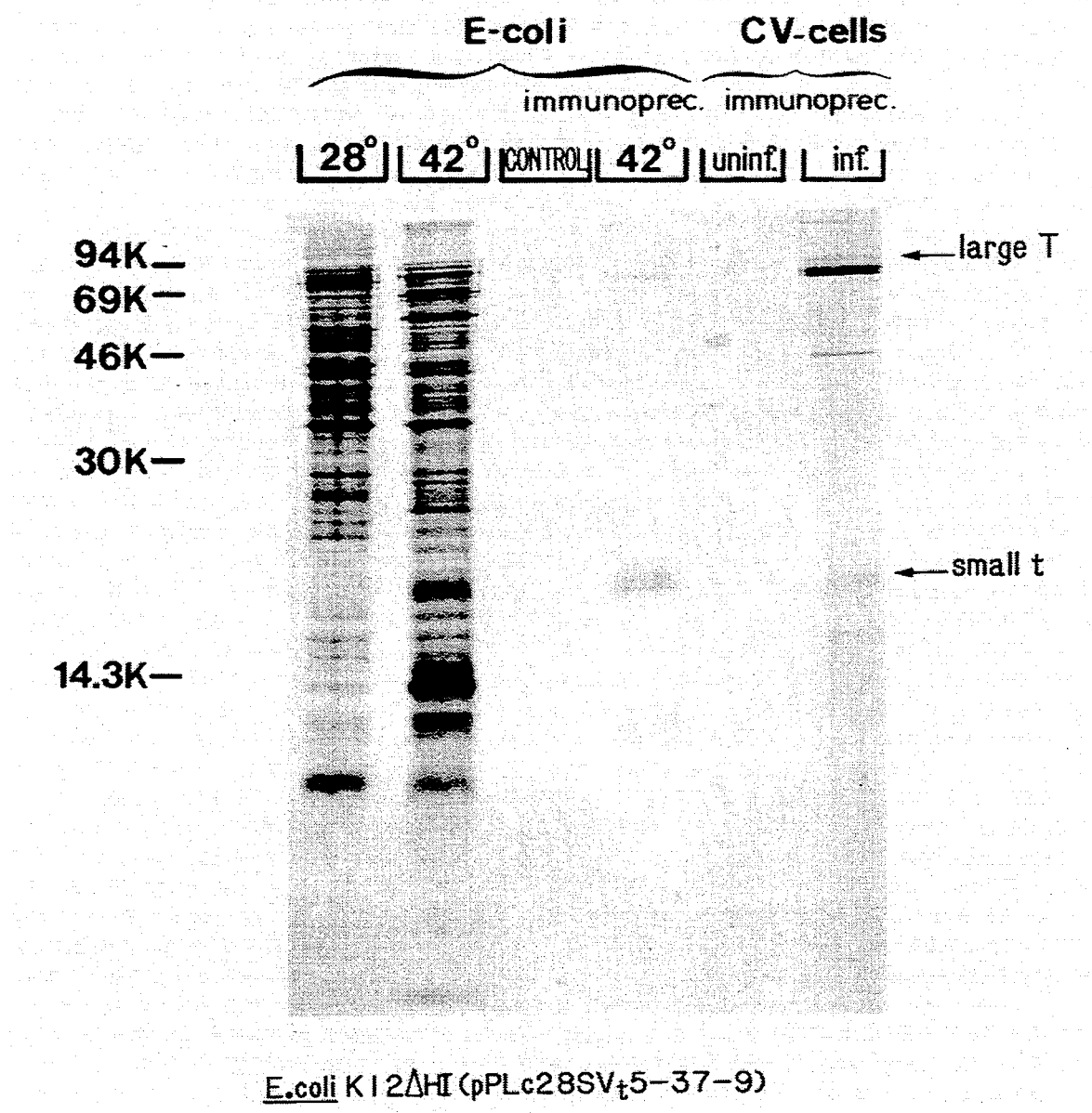
FIG. 14 is an autoradiograph monitoring the protein synthesis at 28° C. and 42° C. of *E. coli* K12ΔHI (pPLc28SV$_t$5-37-9) and the immunoprecipitation with serum from an SV40-tumor-bearing hamster of the proteins synthesized from this host after induction at 42° C. as compared with immunoprecipitation of authentic small-t antigen synthesized in SV40-infected African green monkey kidney cells with the same antiserum.

Transformation of $E.$ $coli$ K12$\Delta$HI with these modified hybrid DNA molecules and induction afforded expression of fairly large amounts of a protein with an apparent molecular weight of 14K (FIG. 14). This protein was not produced without induction and was not produced by host cells that had not been transformed with vectors containing SV40 DNA.

Although authentic small-t antigen has a molecular weight of 19K and the protein produced in these transformed cells was precipitated only very poorly by antibodies raised against the large-T antigen of SV40, two dimensional finger prints (electrophoesis at pH 3.5, followed by chromatography in butanol/acetic acid/pyridine/water (15:3:10:12)) of tryptic peptides derived from this protein and authentic small-t antigen confirmed that the two were related. While not wishing to be bound by theory, it may be that the secondary structure of the mRNA starting at the P$_L$ promoter is such that initiation at an internal initiating codon of small-t antigen is favored over initiation at the true start signal. This hypothesis is also consistent with the secondary structure that could be derived, using the procedures of D. Iserentant & W. Fiers, "Secondary Structure Of mRNA And Efficiency Of Translation Initiation", Gene, 9 pp. 1–12 (1980), from the nucleotide sequences of some of these SV$_t$ containing vectors.

One of the modified pPLc28SV$_t$5 recombinant DNA molecules, prepared as above, expressed minor amounts of a 17K component in addition to the major 14K protein component. This molecule was designated pPLcSV$_t$5-37. While the presence of the 17K protein could only be initially detected by specific immunoprecipitation with large-T antiserum, further modification of the molecule permitted enhanced synthesis of the 17K component. This modification, which consisted of cleaving pPLc28SV$_t$5-37 with EcoRI, extending the recessed 3' ends with DNA polymerase I (K. Backman et al., supra) and religating the blunt ends, may have changed the secondary structure of the mRNA. Hosts transformed with pPLc28SV$_t$5-37-9 afforded approximately 4% of their total de novo protein synthesis as a 17K protein component upon induction. These results are displayed in FIG. 14. As shown in line c of FIG. 14, the 17K component was immunoprecipitated with serum from an SV40-tumor-bearing hamster to substantially the same extent as authentic small-t antigen grown in SV40-infected African green monkey kidney cells.

(b) The Human Fibroblast Interferon (HFIF) Gene

As described in British patent application 80.18701 filed Jun. 6, 1980, the gene coding for human fibroblast interferon was inserted into vectors pPLa8 and pPLc24 to produce recombinant DNA molecules that are capable in transformed hosts after appropriate induction of expressing proteins having an antiviral, physio-chemical, immunlogical and biological activity closely corresponding to authentic human fibroblast interferon.

(c) An FMDV Antigen Gene

As described in British patent application 80.26661, filed Aug. 15, 1980, a DNA sequence coding for a polypeptide displaying the specificity of FMD viral antigens was inserted into vector pPLc24 to produce recombinant DNA molecules that are capable in transformed hosts after appropriate induction of expressing polypeptides having the specificity of FMD viral antigens.

Microorganisms and vectors prepared by the processes described herein are exemplified by cultures deposited in the American Type Culture Collection, Rockville, Md., United States on Sep. 8, 1980 and identified as PL-A to PL-D:

A. *E. coli* M5219 (pPLa2311)
B. *E. coli* K12ΔHI (pPLa8)
C. *E. coli* K12ΔHI (pPLc28)
D. *E. coli* M5219 (pPLc24)

These cultures were assigned accession numbers ATTC 31694-31697, respectively.

In addition, microorganisms and vectors prepared by the processes described herein and also containing inserted DNA sequences for expression therein are exemplified by cultures deposited in culture collection Deutsche Sammlung von Mikroorganismen in Gottingen, West Germany and identified as follows:

HFIF-D: *E. coli* M5219 (G-pPLa-HFIF-67-12) [DSM 1851]

HFIF-E: *E. coli* K12ΔHI (G-pPLa-HFIF-67-12) [DSM 1852]

HFIF-F: *E. coli* M5219 (G-pPLa-HFIF-67-12A19) [DSM 1853]

HFIF-G: *E. coli* M5219 (G-pPLc-HFIF-67-8) [DSM 1854]

FMDV-A: *E. coli* W6 ($\lambda_{rex}$—pPL-VPi-1) [DSM 1879]

FMDV-B: *E. coli* NF1 ($\lambda$N⁻cro⁻cI$_{ts}$-pPL-VPl-1) [DSM 1880]

FMDV-C: *E. coli* NF1 ($\lambda$N⁻cro⁻cI$_{ts}$-pPL-VP1-5) [DSM 1881].

Cultures HFIF-D—HFIF-G were deposited on Jun. 5, 1980.

Cultures FMDV-A—FMDV-C were deposited on Jul. 31, 1980.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than the specific embodiments which have been presented hereinbefore by way of example.

We claim:

1. A method for using a recombinant DNA molecule to produce a polypeptide, the method comprising the steps of:

culturing a host transformed with the recombinant DNA molecule, the molecule comprising a DNA sequence comprising the leftward promoter and operator derived from bacteriophage λ, $P_LO_L$, and a DNA sequence coding for the polypeptide, the DNA sequence coding for the polypeptide being inserted into an endonuclease recognition site in the molecule, the site being located less than 300 base pairs downstream from $P_LO_L$ and located upstream of any sequences of λ DNA downstream of the HaeIII site (73.1%) that may be present in the molecule; and collecting the polypeptide.

2. The method according to claim 1, wherein said recombinant DNA molecule has no active cro gene and no active N gene.

3. The method according to either one of claims 1 or 2, wherein said polypeptide is selected from the group consisting of leukocyte interferon, fibroblast interferon, immune interferon, insulin, human growth hormone, animal growth hormone, antigens of hepatitis and antigens of foot and mouth disease.

* * * * *